United States Patent
Farina et al.

(10) Patent No.: US 9,140,376 B2
(45) Date of Patent: Sep. 22, 2015

(54) ROTARY SHEAR VALVE WITH THREE-POINT STATOR SEATING

(75) Inventors: Edward Francis Farina, Lincoln University, PA (US); Nicholas Michael Shmel, Jr., Elkton, MD (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 149 days.

(21) Appl. No.: 14/117,094

(22) PCT Filed: May 11, 2012

(86) PCT No.: PCT/US2012/037444
§ 371 (c)(1),
(2), (4) Date: Nov. 12, 2013

(87) PCT Pub. No.: WO2012/158490
PCT Pub. Date: Nov. 22, 2012

(65) Prior Publication Data
US 2015/0129071 A1      May 14, 2015

Related U.S. Application Data

(60) Provisional application No. 61/485,782, filed on May 13, 2011.

(51) Int. Cl.
| F16K 11/074 | (2006.01) |
| F16K 27/06 | (2006.01) |
| G01N 35/10 | (2006.01) |
| F16K 5/04 | (2006.01) |
| F16K 11/085 | (2006.01) |

(52) U.S. Cl.
CPC ............... *F16K 27/065* (2013.01); *F16K 5/045* (2013.01); *F16K 5/0464* (2013.01); *F16K 11/0743* (2013.01); *F16K 11/085* (2013.01); *G01N 35/1097* (2013.01); *Y10T 403/74* (2015.01)

(58) Field of Classification Search
CPC .................... F16K 11/0743; Y10T 137/86533; Y10T 137/86863; G01N 35/1097; G01N 2030/201; G01N 2030/202
See application file for complete search history.

(56) References Cited

U.S. PATENT DOCUMENTS

| 2,994,340 | A |   | 8/1961  | Biello et al. |
| 3,297,053 | A | * | 1/1967  | McKinney ............... 137/625.46 |
| 3,439,623 | A |   | 4/1969  | Dietrich et al. |
| 3,537,680 | A | * | 11/1970 | Zajac ............................ 251/172 |

(Continued)

OTHER PUBLICATIONS

PCT International Search Report and Written Opinion dated Aug. 14, 2012 (11 Pages).

*Primary Examiner* — John Fox
(74) *Attorney, Agent, or Firm* — Pepper Hamilton LLP

(57) ABSTRACT

A rotary shear valve having three-point stator seating is provided. Three contact points are predetermined between a bottom of the stator and a valve body rim and three clamping pads may also be predetermined. The three clamping pads and the three points of contact between stator and the valve body rim are corresponding and aligned when the rotary shear valve is assembled so that the clamping or compression forces on both sides of the stator directly oppose one another, thereby effectively canceling each other. In one embodiment, the stator includes three contact points on the bottom surface proximate the periphery of the stator to contact the valve rim and a gasket includes three clamping pads proximate the periphery of the gasket web to apply a compression force on the top surface of the stator above the three contact points.

20 Claims, 35 Drawing Sheets

(56) References Cited

U.S. PATENT DOCUMENTS

| | | | |
|---|---|---|---|
| 3,556,151 A * | 1/1971 | Masuda | 137/625.21 |
| 4,284,920 A | 8/1981 | Nelson | |
| 4,318,218 A | 3/1982 | Nelson | |
| 4,507,977 A | 4/1985 | Cabrera | |
| 6,133,666 A | 10/2000 | Hollenbeck | |
| 6,267,143 B1 * | 7/2001 | Schick | 137/625.11 |
| 7,377,291 B2 * | 5/2008 | Moon et al. | 137/625.46 |
| 7,878,217 B2 | 2/2011 | Buechel | |
| 8,622,086 B2 * | 1/2014 | Servin | 137/625.46 |
| 8,876,081 B2 * | 11/2014 | Tower | 251/208 |
| 2001/0023995 A1 | 9/2001 | Nguyen et al. | |
| 2005/0069454 A1 | 3/2005 | Bell et al. | |
| 2005/0129584 A1 | 6/2005 | Johnson et al. | |
| 2007/0028971 A1 | 2/2007 | Wagner | |
| 2009/0074625 A1 | 3/2009 | Johnson et al. | |
| 2010/0281959 A1 | 11/2010 | Berndt | |
| 2011/0203678 A1 | 8/2011 | Servin | |
| 2012/0119128 A1 | 5/2012 | Moeller | |

* cited by examiner exemplaryExample

ROTARY SHEAR VALVE WITH THREE-POINT STATOR SEATING

CROSS-REFERENCE TO RELATED APPLICATIONS

This application claims priority to U.S. provisional application Ser. No. 61/485,782 filed May 13, 2011, which is incorporated herein by reference in its entirety.

TECHNOLOGY FIELD

The present invention relates in general to fluid control valves and, more particularly, to a rotary shear valve with three point stator seating. Embodiments of the present invention are particularly well suited for, but in no way limited to, fluid control applications requiring rapid selection of fluids with minimal dead-volume in the stator, such as diagnostic test equipment and instruments.

BACKGROUND

Fluid flow control valves are commonly employed in diagnostic instruments to regulate fluids through the device. Operation of the flow control valve is important to ensure proper operation of the diagnostic system. This is especially true in systems having multiple fluids that must be selected quickly during operation. Rotary shear valves are one type of fluid flow control valve and have long been a standard design for flow control used in precision flow control applications. A conventional rotary shear valve includes a generally disc-shaped rotor in contact with a disc-shaped stator. A typical rotary shear valve comprises a stator having one or more ports (e.g., through holes) and a rotor having one or more slots. For example, the stator may include a common port, a sample port, one or more fluid ports, and a waste port. The rotor rotates with respect to the stator to selectively fluidly connect ports of the stator via a slot on the rotor. Exemplary rotary shear valves are disclosed in U.S. Pat. No. 3,567,389 to Coulter et al.; U.S. Pat. No. 3,567,390 to Rothermel; and U.S. Pat. No. 4,507,977 to Cabrera.

In operation, the rotary shear valve may be mounted to a fluid manifold and the rotor may rotate to establish a fluid pathway through the rotary shear valve comprising select stator ports and a rotor slot. The fluid pathway may connect a fluid source to a fluid mixing chamber on the manifold, for example. When the rotor rotates to close off the pathway, the supply side of the stator will have an unmixable volume of fluid. The volume of the unmixable fluid is dependent on the size of the stator port. For example, where the stator ports are circular through holes, the volume of unmixable fluid will be substantially equal to $\pi r^2 h$, where r=radius of circular face of the port, and h=height or thickness of the stator. This unmixable volume of fluid is undesirable.

One way of reducing the unmixable volume of fluid is to reduce the thickness of the stator. A problem with reducing the thickness of the stator, however, is that a thinner stator has a tendency to deform when clamped or forced against a valve housing surface. Deformation of the stator causes the valve to leak, which is also undesirable. For this reason, conventional stators tend to be relatively thick (e.g., greater than 3 mm). As described above, a thicker stator results in an undesirable larger volume of unmixable fluid.

Deformation of the stator in a rotary shear valve due to a clamping force may result from the following condition. One conventional design approach is to have a clamping force on both sides (e.g., top and bottom) and around the entire periphery of the stator. For example, a stator seating force on the top side of the stator may be provided by an o-ring that acts to seat a bottom surface of the stator against a relatively flat valve housing rim. In a typical design, the stator is made from a ceramic material and includes a highly polished flat surface, and the valve housing rim is made of metal. Although attempts are made to ensure an equal and opposite force around the entire periphery of the stator, the fact is that the metal surface of the valve housing rim is not completely flat, at least not when compared to the highly polished flat surface of the ceramic stator. As such, the stator seating o-ring force around the entire top periphery of the stator seats the stator against the three highest points of the valve housing rim and the stator deforms like a potato chip. This results in undefined and random contact mounting deformation between the stator and rotor. This condition may lead to leaking of the rotary shear valve.

Another problem with some conventional rotary shear valves is that they include a valve housing having an upper and bottom stator seating rim. These designs require a large, heavy spring to properly seat the stator and to provide adequate sealing force between the rotor and the stator. Large, heavy springs also typically require use of a relatively thick stator. In addition, a large, heavy spring also results in higher torque requirements to rotate the rotor, which requires a larger, more powerful motor. This may also lead to a reduction in the valve switching speed, which is also undesirable.

In other conventional designs, the stator may be top loaded. For example, a compression force may be asserted on top of the stator to seat the bottom of the stator on the valve body rim. In such conventional rotary shear valves, the stator is permanently affixed to the structure to which it is mounted (e.g., a fluid manifold). For example, an epoxy is used to permanently affix and seal the stator to the manifold. This is undesirable since any failure of the valve requires replacement of both the rotary shear valve and the manifold. Also, over time the epoxy will degrade and lose its bond causing delamination of the epoxy and valve failure.

SUMMARY

Embodiments of the present invention address and overcome the above shortcomings and drawbacks by providing an improved rotary shear valve with three-point stator seating. This three-point stator seating at predetermined contact points between the stator and valve housing rim allows the use of a stator having a minimum stator thickness while still preventing leakage of fluid between the stator and rotor. Minimizing the thickness of the stator minimizes the unmixed volume of fluid on the supply side of the stator. This technology is particularly well-suited for, but by no means limited to, rotary shear valves used with diagnostic test equipment and instrumentation.

According to one embodiment of the invention, the stator seating forces are applied at three predefined points where the stator contacts the valve housing. This provides a near net zero deflection and/or deformation of the stator, thereby allowing a thin stator to be used while still reducing and/or preventing leakage. In some embodiments, the stator has a thickness of less than about 3 mm. Three contact points can be achieved by providing three points on the stator, or three points on the valve housing rim, or both.

The three points of contact are preferably located on the component, which lends itself to the easiest fabrication. In some embodiments, the three contact points are formed on the ceramic stator. According to one embodiment of the invention, three contact points are integrally formed with the stator.

According to another embodiment, three contact points are integrally formed with the valve housing rim.

According to one embodiment of the invention, three contact points are substantially 120 degrees apart around the periphery of the bottom surface of the stator. According to another embodiment of the invention, three contact points form an isosceles triangle. In such embodiment, imaginary lines connecting the three contact points form an isosceles triangle, wherein a second contact point and a third contact point are substantially equal distance around the stator periphery from a first contact point. In some embodiments, the two angles having the same measure are between about 65 degrees and about 85 degrees. In another embodiment, the three contact points form a scalene triangle wherein the angles between the three points are all different around the periphery of the stator.

According to one embodiment of the invention, three clamping pads are provided for top loading the top surface of the stator. In one embodiment, a gasket is provided having three clamping pads that correspond to, and are aligned with, the three contact points between the stator and the valve body rim. According to one embodiment of the invention, the manifold includes three clamping pads that correspond to, and are aligned with, the three contact points between the stator and the valve body rim. According to another embodiment of the invention, the three contact points are formed on the stator and the three clamping pads are formed on the gasket.

According to another embodiment of the invention, a rotary shear valve comprises a valve body having a motor mount end and a manifold mount end. A cavity extends through the valve body between the motor mount end and the manifold mount end. A valve body rim is formed in the cavity. A disc-shaped rotor is rotatably mounted in the valve body, the rotor comprising: one or more slots in a top surface; and a rotor sealing face on the top surface. A disc-shaped stator is mounted in the valve body, the stator comprising: a top surface and a bottom surface; one or more ports extending between the top surface and the bottom surface; a stator sealing face on the bottom surface, wherein the stator sealing face is in sliding and sealing contact with the rotor sealing face; and an annular recess in an outer periphery of the bottom surface of the stator. Three predefined contact points are defined between the stator annular recess and the valve body rim, wherein the stator only contacts the valve body rim at the three contact points.

According to an aspect of the invention, the three predefined contact points are integrally formed with the stator. According to an aspect of the invention, the three predefined contact points are formed as extensions of the bottom surface of the stator into the annular recess. According to an aspect of the invention, the three predefined contact points are formed as high points on the annular recess of the stator. According to an aspect of the invention, the three contact points are integrally formed with the valve body rim.

According to an aspect of the invention, the rotary shear valve further comprises three clamping pads for contacting the top surface of the stator, wherein the three clamping pads correspond to, and are aligned with, the three contact points such that forces on the stator top surface and the stator bottom surface are equal and oppose, and substantially cancel one another out. According to an aspect of the invention, the rotary shear valve includes a gasket having a gasket web, wherein the three clamping pads are integrally formed with the gasket web, and the three clamping pads contact the top surface of the stator above the three contact points.

According to an aspect of the invention, the rotary shear valve further comprises an alignment feature to ensure proper alignment and orientation of the stator in the valve body. In some embodiments, the alignment feature comprises a notch on the stator and an arm on the valve body, wherein the arm is received within the notch when the stator is inserted into the rotary shear valve.

According to another embodiment of the invention, a rotary shear valve comprises a valve body having a motor mount end, a manifold mount end, a cavity extending between the motor mount end and the manifold mount end, and a valve body rim. The valve body rim includes an inner diameter and a valve body rim seating surface. A motor may be mounted to the motor mount end, the motor having an output shaft extending into the cavity. A cup is disposed within the cavity. A spring is disposed within the cup such that a first end of the spring contacts the cup. A thrust bearing is disposed on a second end of the spring. A disc-shaped rotor is rotatably disposed within the valve body. The rotor includes a rotor top surface having a rotor sealing face, a rotor sleeve, and a rotor drive shaft. The rotor drive shaft extends through the thrust bearing, the spring, and the cup, and a first end of the rotor drive shaft is connected to the motor output shaft. The rotor sleeve contacts the thrust bearing, and the rotor sealing face is disposed within the inner diameter of the valve body rim. One or more fluid slots is provided in the top surface of the rotor. A disc-shaped stator is mounted in the valve body proximate the rotor. The stator includes a stator top surface and a stator bottom surface, and a plurality of fluid ports extending between the stator top surface and the stator bottom surface. A stator includes a sealing face on the stator bottom surface, wherein the stator sealing face is in sliding and sealing contact with the rotor sealing face. The stator also includes an annular recess in an outer periphery of the stator bottom surface. Further, the stator comprises three contact points defined between the stator annular recess and the valve body rim seating surface. The stator only contacts the valve body rim at the three contact points.

According to another aspect of the invention, the valve body further comprises a motor mount and a manifold mount. The motor mount comprises a motor mount first end, a motor mount second end, and a motor mount cavity extending between the motor mount first end and the motor mount second end. The manifold mount comprises a manifold mount first end, a manifold mount second end, and a manifold mount cavity extending between the manifold mount first end and the manifold mount second end. The manifold mount first end is connected to the motor mount second end.

According to another aspect of the invention, the rotary shear valve includes a gasket in contact with the stator top surface. The gasket includes a gasket body and a plurality of gasket fluid ports. In some embodiments, the gasket body generally corresponds in size and shape to the stator. The gasket fluid ports correspond in number and location to the stator fluid ports. An o-ring may be provided around a perimeter of each of the gasket fluid ports. The gasket may include three clamping pads disposed near the periphery of the gasket body. The three clamping pads correspond to, and are aligned with, the three contact points of the stator when the gasket is in contact with the stator top surface.

According to another embodiment of the invention, a rotary shear valve is provided having a disc-shaped body having a top surface, a bottom surface, and a side wall extending between the top surface and the bottom surface. One or more ports is provided extending between the top surface and the bottom surface. A disc-shaped sealing face is provided in a center region of the bottom surface. An annular recess is provided in an outer periphery of the bottom surface and surrounding the disc-shaped sealing face. Three predefined contact points are provided in the annular recess, the three contact points raised above the annular recess. In some embodiments, the three contact points comprise three predefined extensions of the disc-shaped sealing face into the annular recess. In some embodiments, a distance between the top surface of the disc-shaped body and the sealing face is greater than the distance between the top surface of the disc-shaped body and the annular recess. In some embodiments, the distance between the top surface of the disc-shaped body and the contact points is substantially equal to the distance between the top surface of the disc-shaped body and the sealing face.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Figure 1:
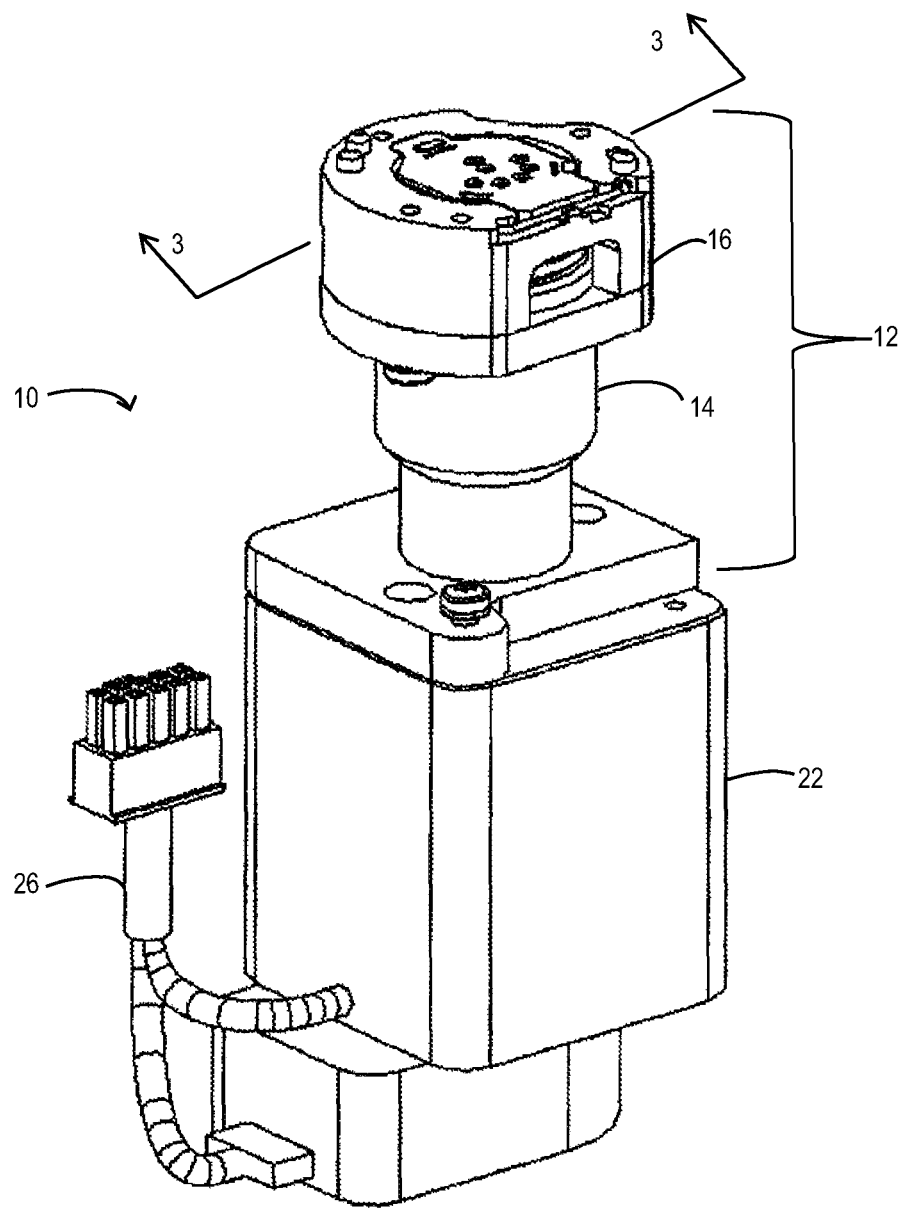
FIG. 1 is a perspective view of an exemplary rotary shear valve.

The above problems and shortcomings in the prior art have motivated the creation of a rotary shear valve having three-point stator seating to ensure a predetermined and adequate seating arrangement of the stator to the valve body. Embodiments of the present invention predetermine three contact points between a first side or bottom of the stator and the valve body rim so that it is known exactly where the ceramic stator will contact the metal valve body rim. Embodiments of the present invention may also predetermine three clamping points for top loading the stator. For example, some embodiments may predetermine three clamping pads between a second side or top of the stator and a manifold to which the rotary shear valve may be connected/mounted. In some embodiments, the three clamping pads between the stator and a manifold and the three points of contact between the stator and the valve body rim are corresponding and aligned so that the clamping or compression forces on both sides of the stator directly oppose one another, thereby effectively canceling each other out and minimizing deformation or warping of the stator. This three point design approach wherein the stator contacts the valve housing at three predefined contact points and a gasket applies a seating force directly above those three contact points, and only at those contact points, results in a net bending force on the stator of substantially zero.

In one preferred embodiment, the stator includes three contact points on the bottom surface proximate the periphery of the stator to contact the valve rim, and a gasket includes three clamping pads proximate the periphery of the gasket web to apply a compression force on the top surface of the stator above the three contact points. The three contact points of the stator and the three clamping pads of the gasket correspond and align with one another when the rotary shear valve is assembled. Also, the three contact points of the stator and the three clamping pads of the gasket preferably generally correspond in size and shape. When the valve is assembled and mounted to a manifold, a top loading force may be generated by the three clamping pads to press down on the top of the stator to seat the three contact points on the bottom of the stator on the valve body rim. Once seated, an equal and directly opposing force results on the bottom of the stator where the three contact points hit the valve body rim.

This design and construction allows for a reduced thickness for the stator (e.g., a thinner stator) than is possible with conventional designs that apply a downward force around the entire periphery on the top of the stator and an upward force at three random places on the bottom of the stator. A thinner stator results in a reduced unmixable volume of fluid on the supply side of the stator. In some embodiments, the stator has a thickness less than about 3 mm. Some embodiments have a stator having a thickness of about 1 mm to about 3 mm.

As used herein, fluid means a continuous, amorphous substance in which molecules move freely past one another and that has a tendency to assume the shape of its container; including a liquid or gas. As used herein, fluids include liquids and gases (e.g., air). Furthermore, as used herein, fluids include reagents and samples (e.g., serum, plasma, and urine samples).

Figure 2:
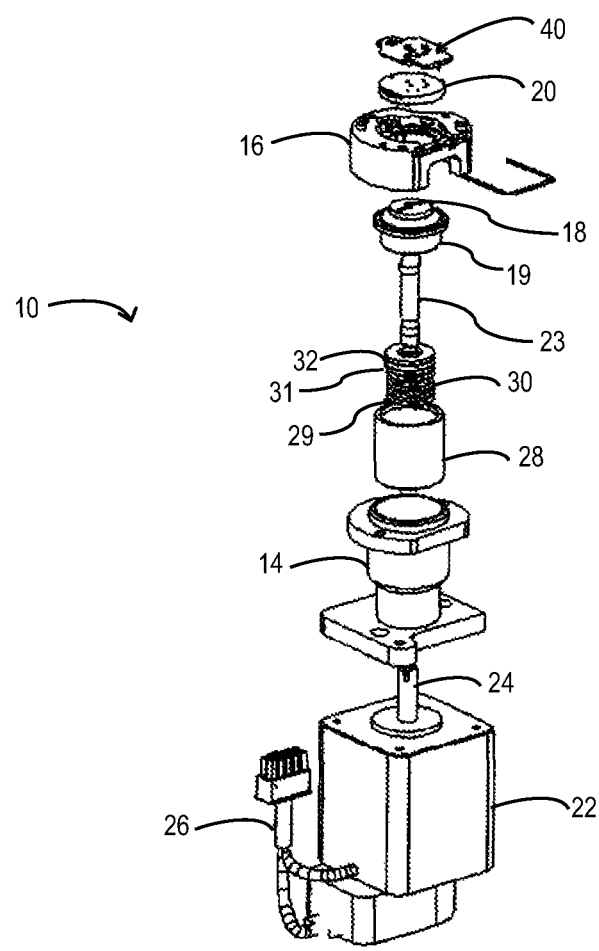
FIG. 2 is an exploded view of the exemplary rotary shear valve.
Figure 3:
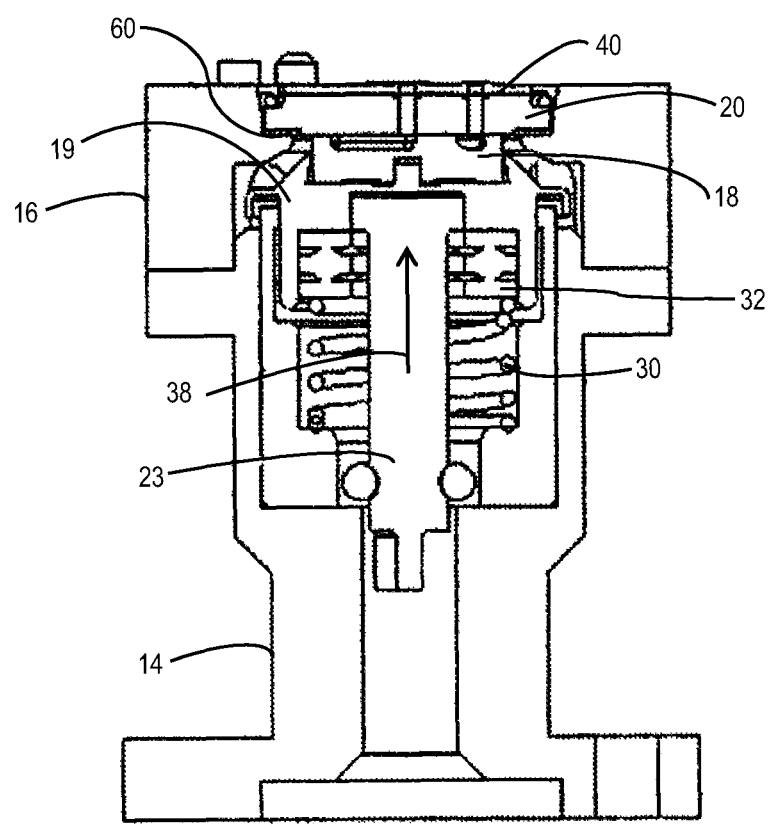
FIG. 3 is a cross sectional view of the exemplary rotary shear valve taken along line 3-3 of FIG. 1.

FIGS. 1-3 show an exemplary rotary shear valve 10. As shown in FIGS. 1-3, the rotary shear valve 10 includes a valve body 12 comprising a motor mount 14 and a manifold mount 16. The valve body 12 houses a rotor 18 and a stator 20. A motor 22 is mounted to the motor mount 14 of the valve body 12. As shown, an output shaft 24 of the motor 22 is operatively coupled to the rotor 18 via a drive shaft 23. The motor 22 may be energized via a power source (not shown) via power cable 26 to rotate the rotor 18 within the valve body 12. The rotor 18 is in sliding contact with the stator 20, which is stationary with respect to the valve body 12.

FIG. 2 is an exploded view of the exemplary rotary shear valve of FIG. 1. As shown in FIG. 2, the rotary shear valve 10 includes a cup 28 that is received in the motor mount 14. A first end 29 of spring 30 is seated in the cup 28 and a thrust bearing 32 is located at a second end 31 of the spring 30. Drive shaft 23 extends through the thrust bearing 32 and spring 30 and operatively couples the motor output shaft 24 to the rotor 18 via a rotor sleeve 19. In operation, the spring 30 exerts a force on rotor 18 to help maintain sealing contact between the rotor 18 and the stator 20. The spring 30 is sized to allow sealed rotation between the contact surfaces of the rotor 18 and stator 20.

FIG. 3 is a cross-sectional view of the valve body 12 of the rotary shear valve 10. As shown in FIG. 3, the assembled valve includes a gasket 40 in contact with the top of the stator 20, the stator 20 in contact with the top of the rotor 18, the rotor 18 mounted on the rotor sleeve 19 which is connected to the rotor drive shaft 23. The thrust bearing 32 fits within a cavity in the rotor sleeve 19 on the opposite side as the stator 20. The compression spring 30 sits within the cup 28 and exerts a force upward (in the direction of arrow 38) on the thrust bearing and, in turn, this force is transmitted to rotor 18 to help form and maintain a seal between the rotor 18 and the stator 20.

Figure 4A:
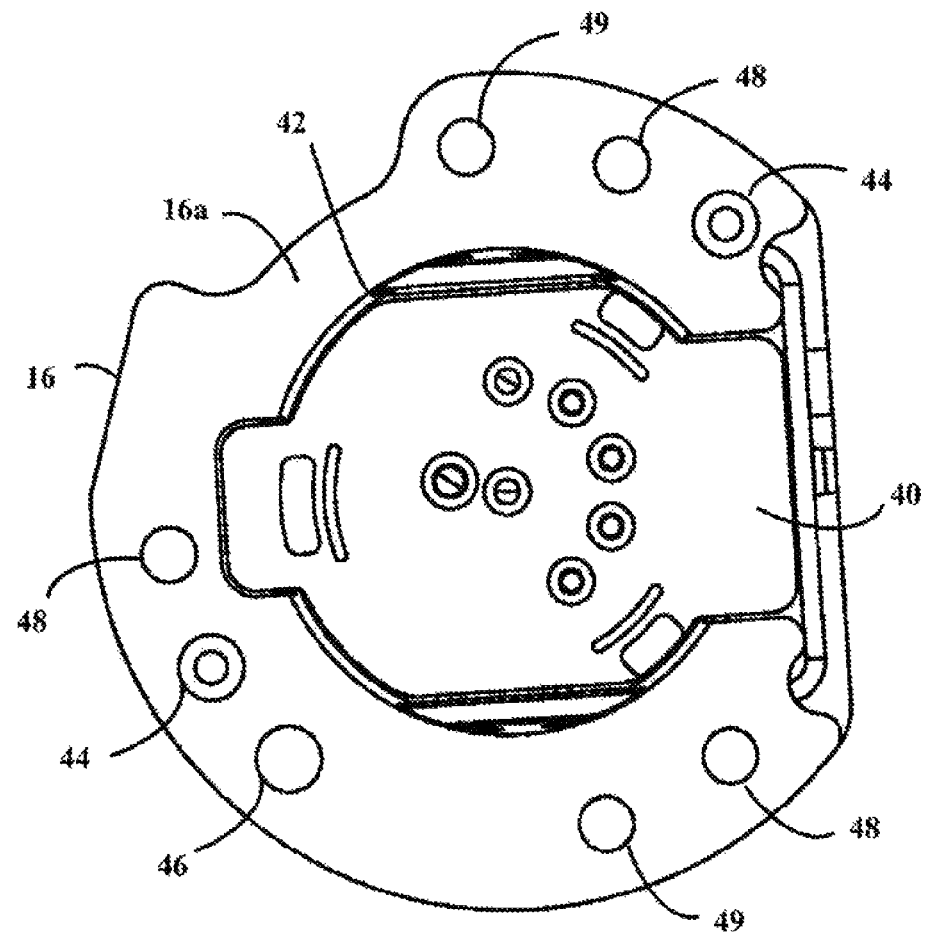
FIGS. 4A and 4B are a top view and a top perspective view, respectively, of an exemplary manifold mount of the exemplary rotary shear valve showing an exemplary gasket.
Figure 4B:
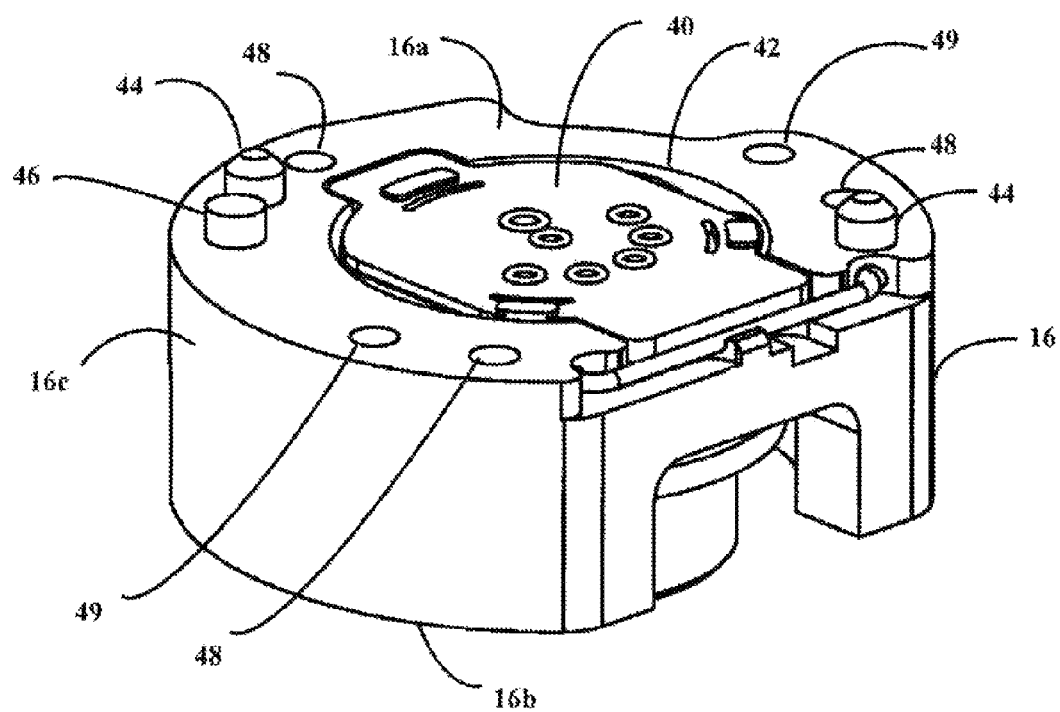

FIGS. 4A and 4B are top and top perspective views, respectively, of the manifold mount 16 of rotary shear valve 10 showing the features of the manifold mount 16 and an exemplary gasket 40. As shown, manifold mount 16 includes a manifold mounting face 16a, a motor mounting face 16b, and a side wall 16c extending between the manifold mounting face 16a and the motor mounting face 16b. An opening or cavity 42 is defined in a center area of the manifold mount 16. As shown, the manifold mount 16 also includes one or more alignment posts 44 extending from the manifold mounting face 16a, a grounding pin 46 extending from the manifold mounting face 16a, a plurality of manifold mounting holes 48 in the manifold mounting face 16a for mounting the manifold mount 16 to, for example, a manifold 144 (see FIG. 15), and a plurality of motor mounting holes 49 in the manifold mounting face 16a. In some embodiments, the manifold mounting holes 48 and/or the motor mounting holes 49 may comprise threaded holes.

Figure 5A:
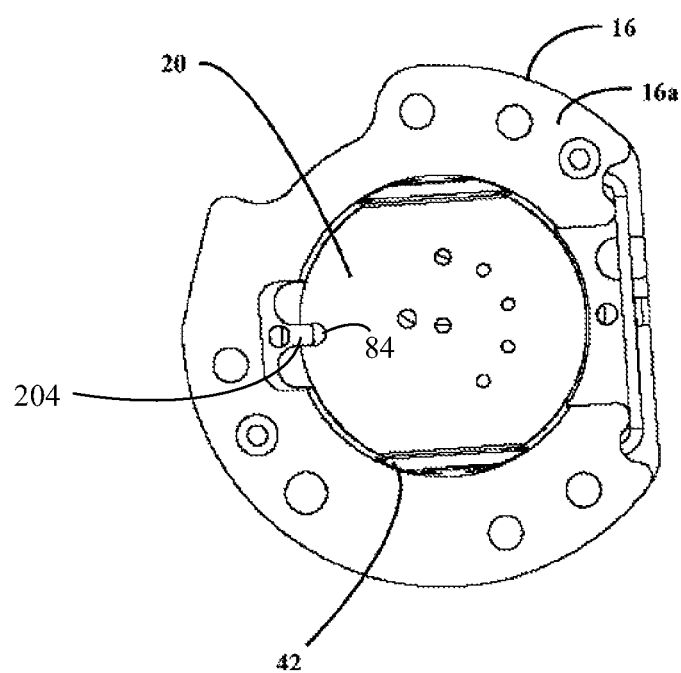
FIGS. 5A and 5B are a top view and a top perspective view, respectively, of the exemplary manifold mount of the exemplary rotary shear valve with the gasket removed and showing an exemplary stator.
Figure 5B:
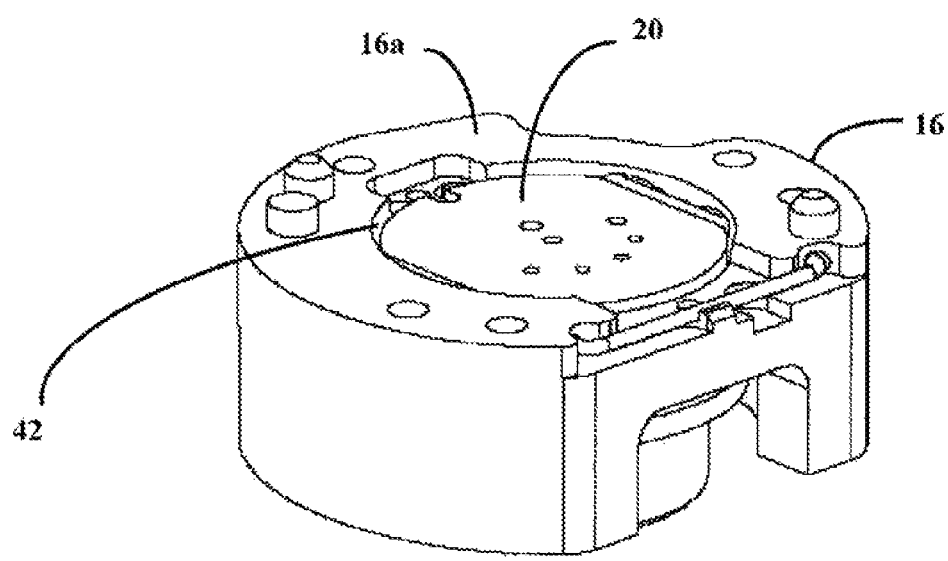

FIGS. 5A and 5B show a top view and a top perspective view, respectively, of the manifold mount 16 of rotary shear valve 10 with the gasket 40 removed and showing an exemplary stator 20. As shown, the stator 20 is mounted within cavity 42 of the manifold mount 16 at a position below the manifold mounting face 16a. The portion of cavity 42 in which stator 20 sits is preferably sized to form a snug fit with minimal radial clearance between the cavity sidewall and the outer diameter of the stator 20. Additional details of the exemplary stator 20 are provided below with reference to FIGS. 8A-8E and additional details of the manifold mount 16 are provided below with respect to FIGS. 10A-10E.

Figure 6A:
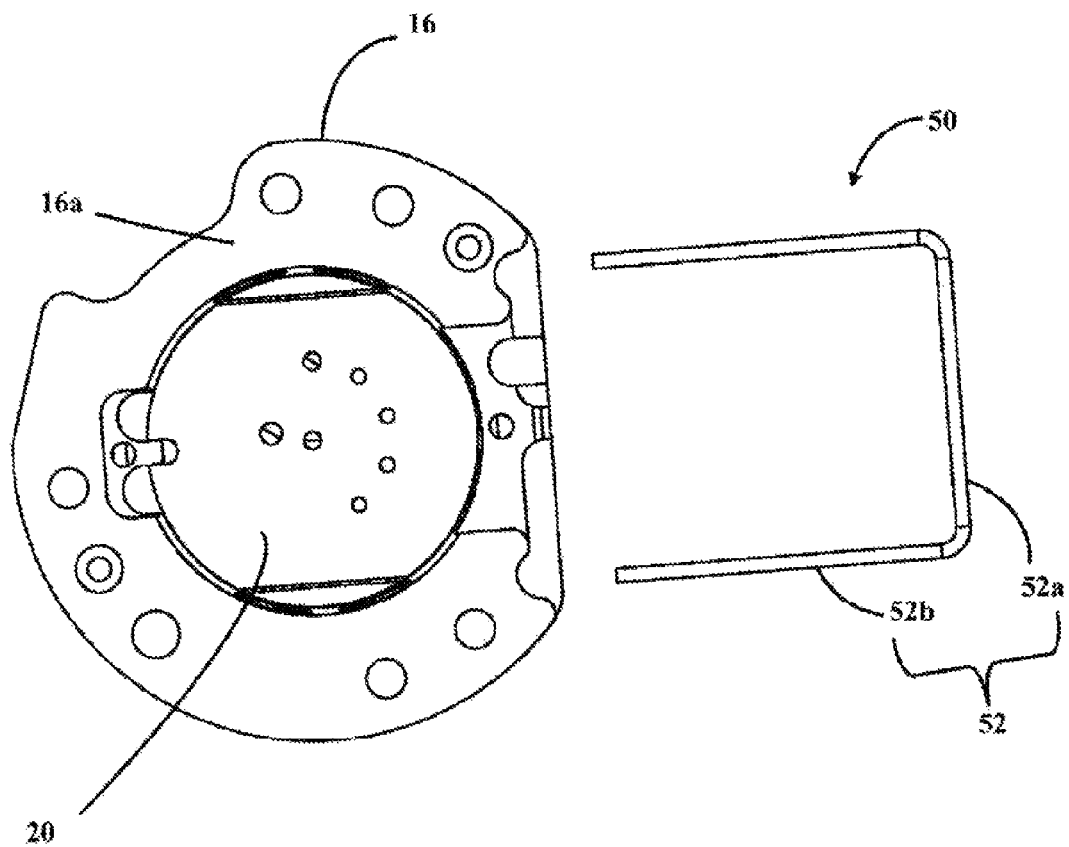
FIGS. 6A and 6B are a top view and a top perspective view, respectively, of the exemplary rotary shear valve showing an exemplary stator retention system.
Figure 6B:
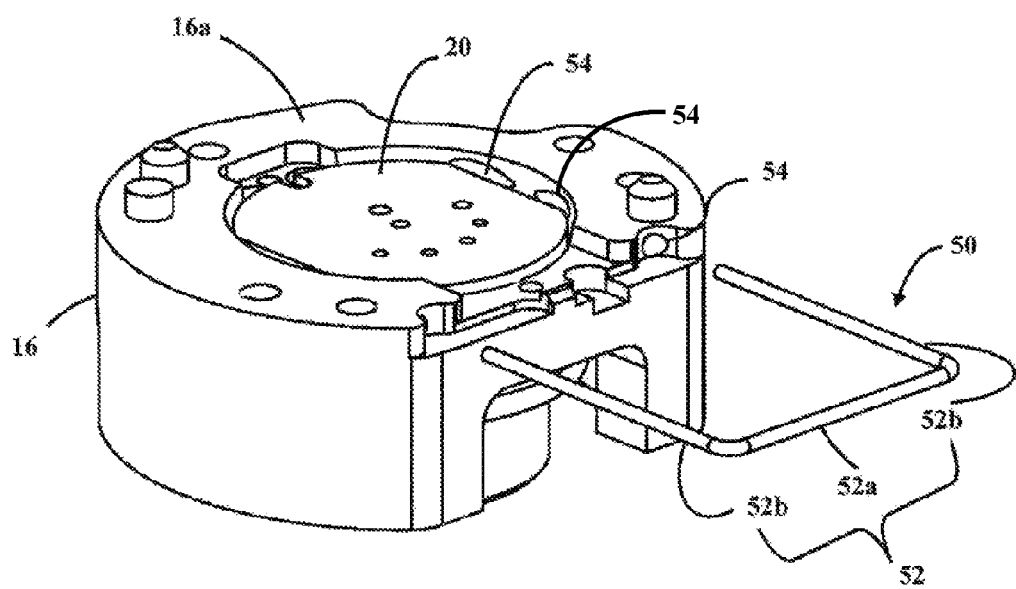

FIGS. 6A and 6B show top and top perspective views, respectively, of the exemplary rotary shear valve showing an optional stator retention system 50. As shown in FIGS. 6A and 6B, one embodiment of the manifold mount 16 includes stator retention system 50 comprising a stator retention clip 52 that may be inserted in stator retention clip holes 54 in the manifold mount 16. As shown in the illustrated embodiment, the stator retention clip 52 comprises a U-shaped member having a base 52a and two legs 52b. The legs 52b are inserted into the stator retention clip holes 54 and function to secure the stator in place within the rotary shear valve body 12.

Figure 15:
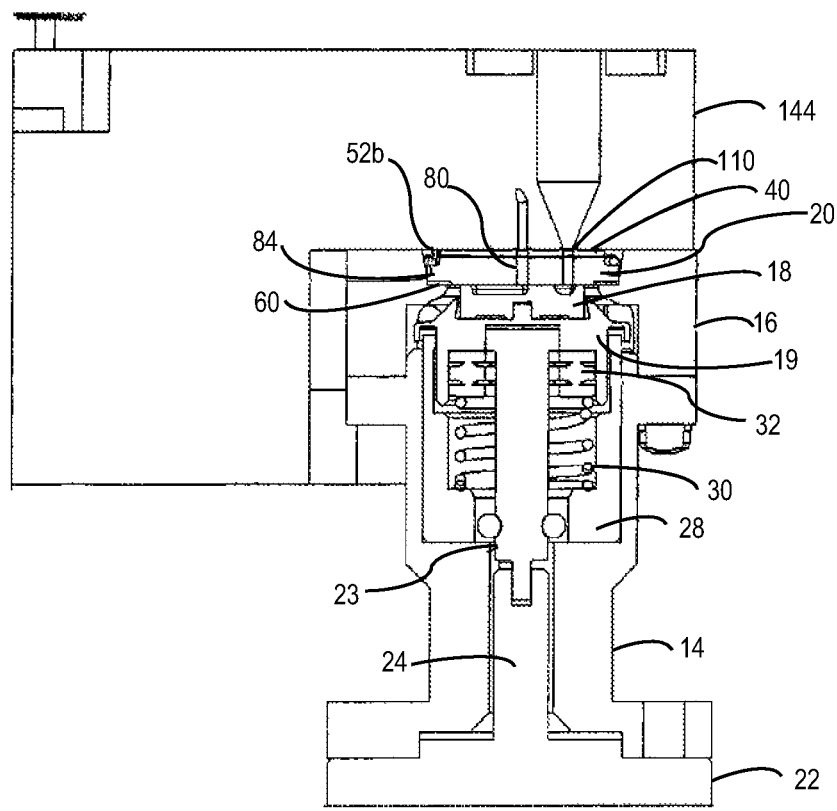
FIG. 15 is a cross-sectional view of the exemplary rotary shear valve and manifold taken along line 15-15 of FIG. 14.

The rotary shear valve having a stator retention system 50 provides a modular design that allows for repair/replacement of the valve and valve ceramics without the need to scrap the acrylic manifold 144 (FIG. 15). In the exemplary embodiment, the ceramic stator 20 is loosely retained in the valve body 12 with the stator retention system 50 as a stainless steel spring clip. This facilitates handling and installation of the rotary shear valve while retaining the stator 20 within the valve body 12, and preventing the stator 20 from falling out of the valve 10. The stator 20 is held in its operating position by the valve gasket 40 which is installed between the valve and the IMT (integrated multi-sensor technology) acrylic manifold (as shown in FIG. 15).

Figure 7A:
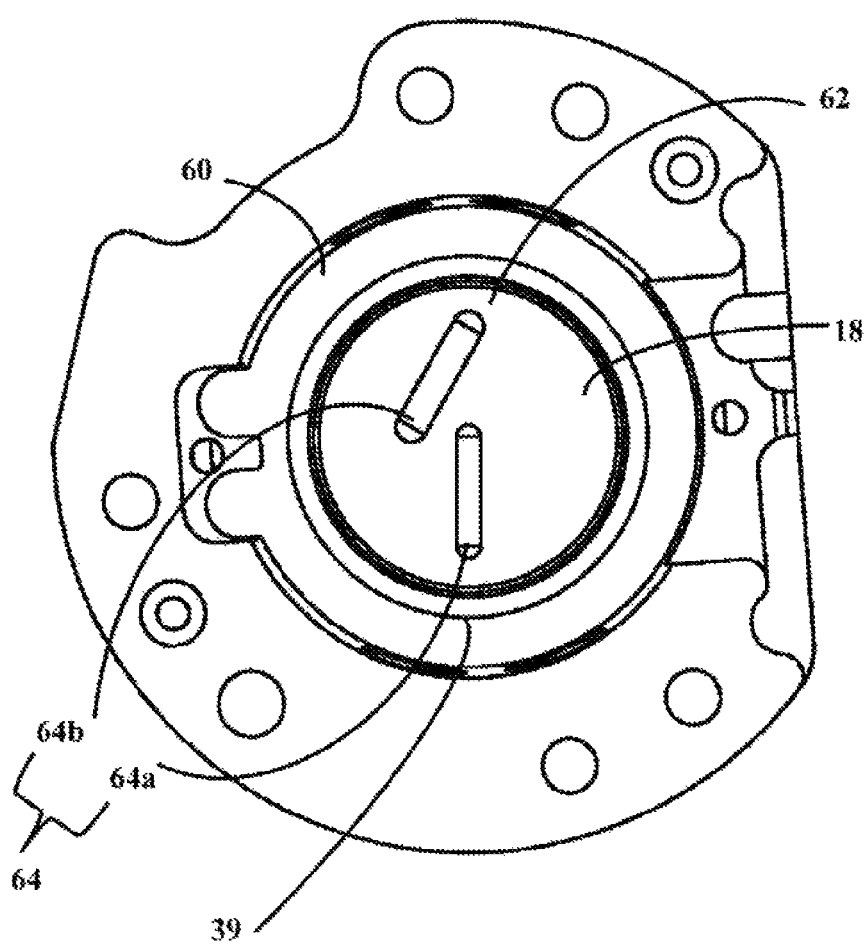
FIGS. 7A and 7B are a top view and a top perspective view, respectively, of the exemplary rotary shear valve with the stator removed and showing an exemplary rotor.
Figure 7B:
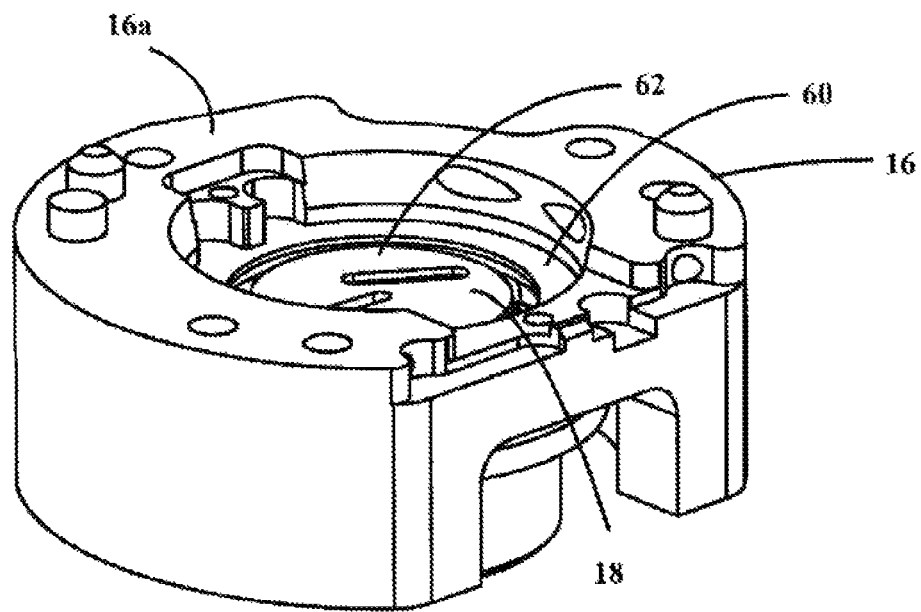

FIGS. 7A and 7B show top and top perspective views, respectively, of the manifold mount 16 of rotary shear valve 10 with the stator 20 removed and showing an exemplary rotor 18. As shown, rotor 18 includes a generally circular or disc-shaped body. As shown, the rotor 18 is mounted within opening 39 of the manifold mount 16 at a position below the manifold mounting face 16a. Opening 39 is defined by an inner diameter of valve body rim 60. As shown, rotor 18 has a diameter less than the diameter of opening 39. As shown, the rotor 18 includes a stator contact surface or seal face 62 for contacting a contact surface or seal face 76a (FIG. 8B) of the stator 20. One or more slots or channels 64 may be formed in the stator mating surface 62. As shown in the exemplary embodiment, the rotor 18 may include two slots 64a and 64b.

The rotor 18 is the rotating component of the rotary shear valve 10. As shown, the rotor 18 includes a sample slot 64a and a waste slot 64b machined into its top contact surface 62. The contact surface 62 includes a sealing face that contacts a sealing face on the contact surface of the stator 20. The sealing faces of the rotor and stator comprise highly polished ceramic surfaces that are substantially flat (e.g., about one wavelength of light). The fluid slots 64 form fluid channels to direct the movement of fluid between the ports on the stator 20. For example, rotation of the rotor 18 may selectively fluidly connect one of the fluid ports with the center or sample port via the fluid slot 64a; or the sample port to the waste port via the waste slot 64b.

In some embodiments, the rotor 18 may include three holes on the back side of the rotor sleeve 19 (not shown). For example, a center one may fit tightly over a post feature of the rotor sleeve 19 to keep the rotor 18 concentric with respect to the rotor sleeve 19, and two others may be used to receive dowel pins (not shown) in the rotor sleeve 19. The recessed areas on the rear of the rotor provide a gap between the rotor 18 and rotor sleeve 19 for the epoxy used to bond the two together.

In some embodiments, the rotary shear valve 10 may use a stepper motor encoder Z-index pulse as its "home sensor." Rotor position may be auto-aligned by system software by, for example, monitoring vacuum pressure of an IMT manifold pressure transducer. During auto-alignment, the offsets from home to each valve position may be learned and backlash in the drive linkage may be measured so it may be accounted for during rotor movements to maintain accurate positioning.

FIGS. 8A-8E show further details of an exemplary stator 20 of the rotary shear valve 10. The stator 20 has three contact points 70 or "arm features" that allow a seating force on top of the stator 20 to be directly transmitted through the stator 20 to the valve manifold mount 16 to minimize any warping of the stator 20. In the illustrated embodiment, the stator's three contact points 70 contact a valve body rim or seat 60, and a clearance or gap exists between the stator annular recess surface 76b and the valve body rim or seat 60 (see e.g., FIGS. 3, 7A, 7B, 8B, 8C, and 8E).

As shown, stator 20 includes a generally circular or disc-shaped body 72 having top surface 74, a bottom surface 76, and a side wall 78. A plurality of ports or through holes 80 are formed in the stator 20. The ports 80 form openings or fluid passageways between the top surface 74 and the bottom surface 76 of the stator 20. As shown, the ports include, for example, seven fluid ports, including: center common port 80a; sample port 80b; vent 1 port 80c; Standard A port 80d; Standard B port 80e; vent 2 port 80f; and a waste port 80g (see FIG. 8A).

Figure 8A:
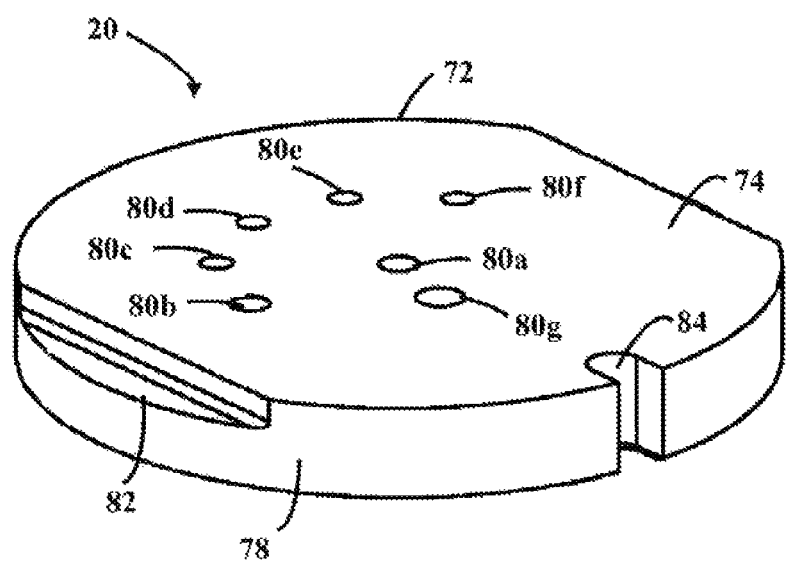
FIGS. 8A-8E show a top perspective, bottom perspective, top, side, and bottom views, respectively, of an exemplary stator of the rotary shear valve of FIG. 1.
Figure 8B:
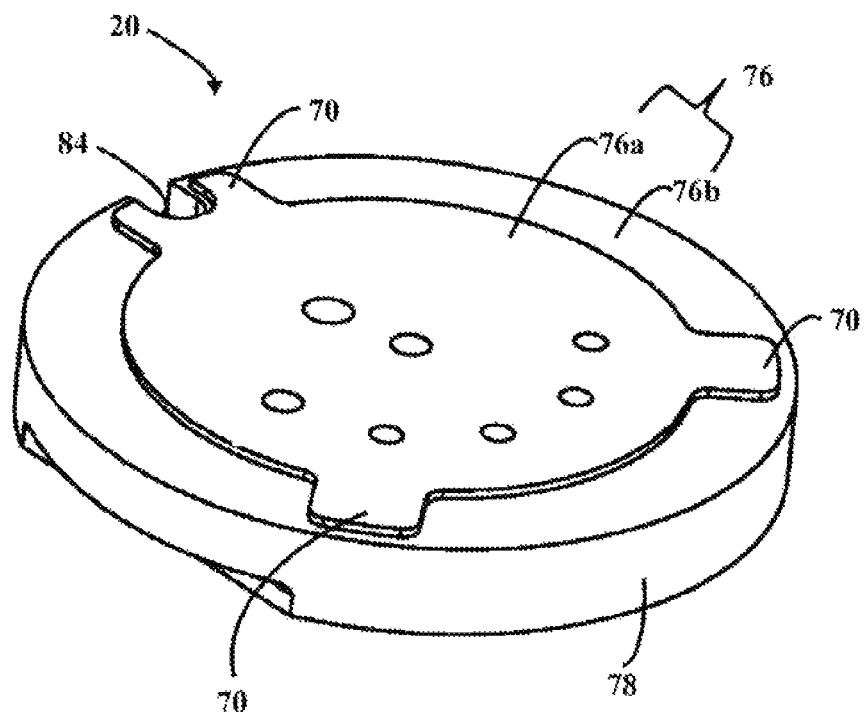
Figure 8C:
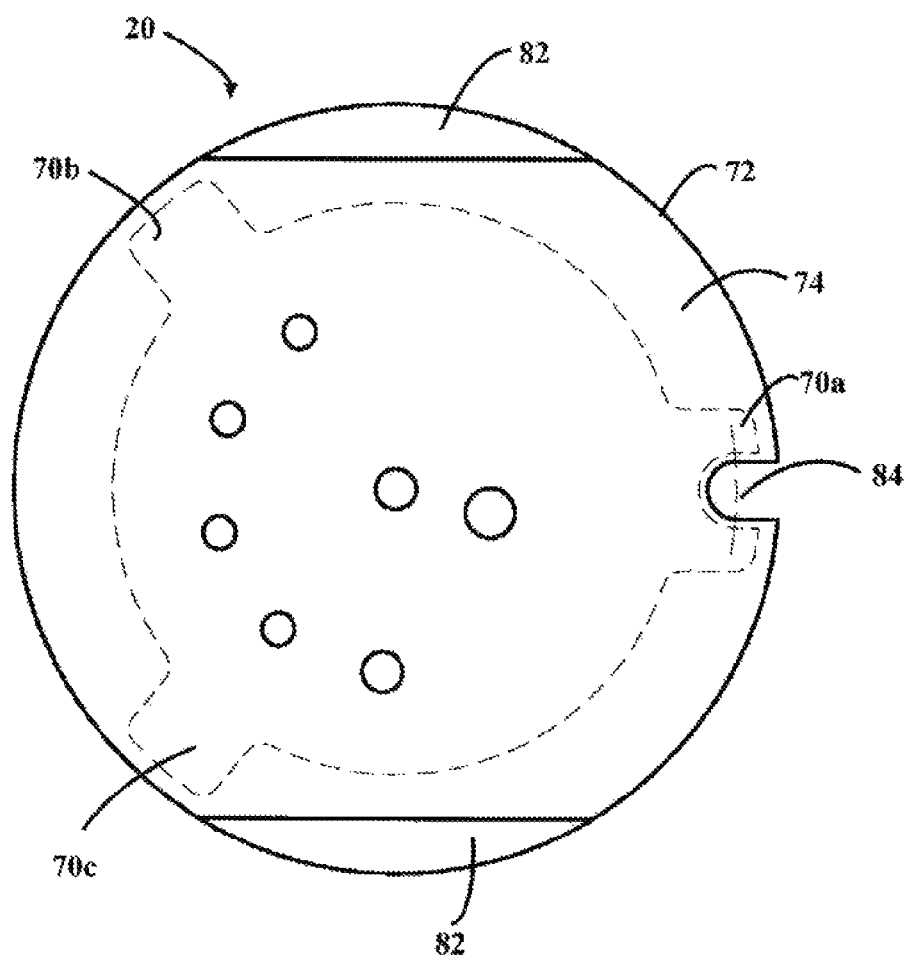
Figure 8D:
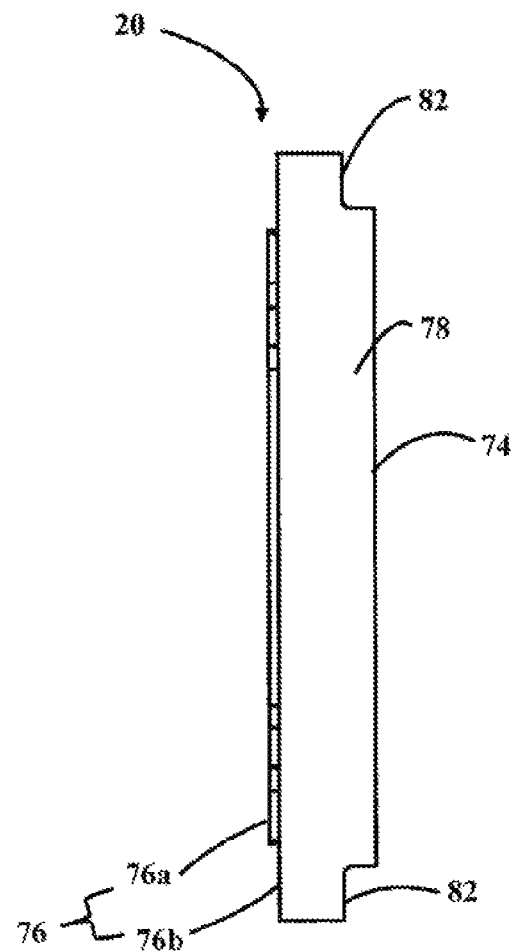
Figure 8E:
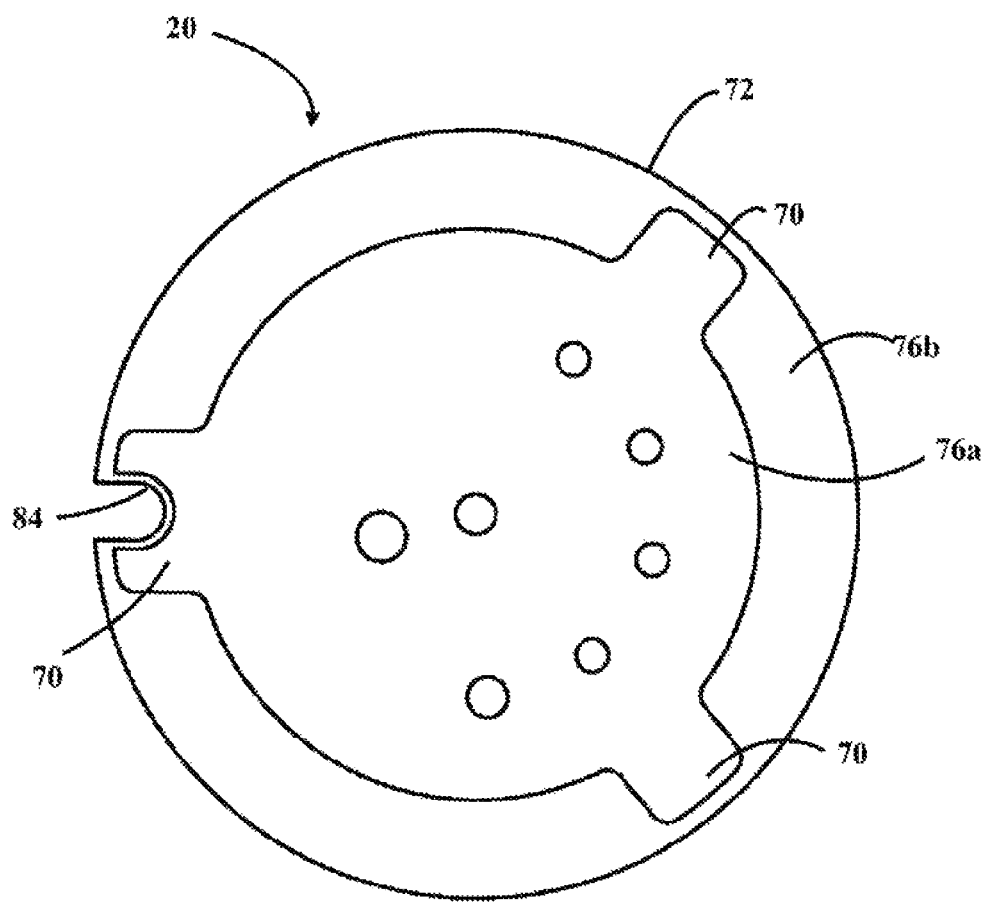
Figure 9A:
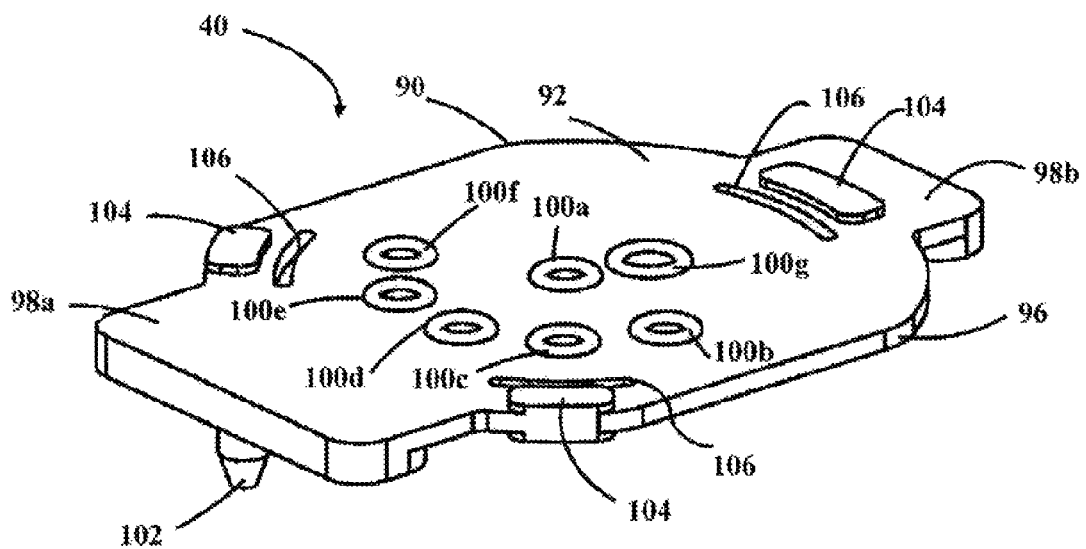
FIGS. 9A-9E show a top perspective, bottom perspective, top, side, and bottom views, respectively, of an exemplary gasket that may be used with the rotary shear valve of FIG. 1.
Figure 9B:
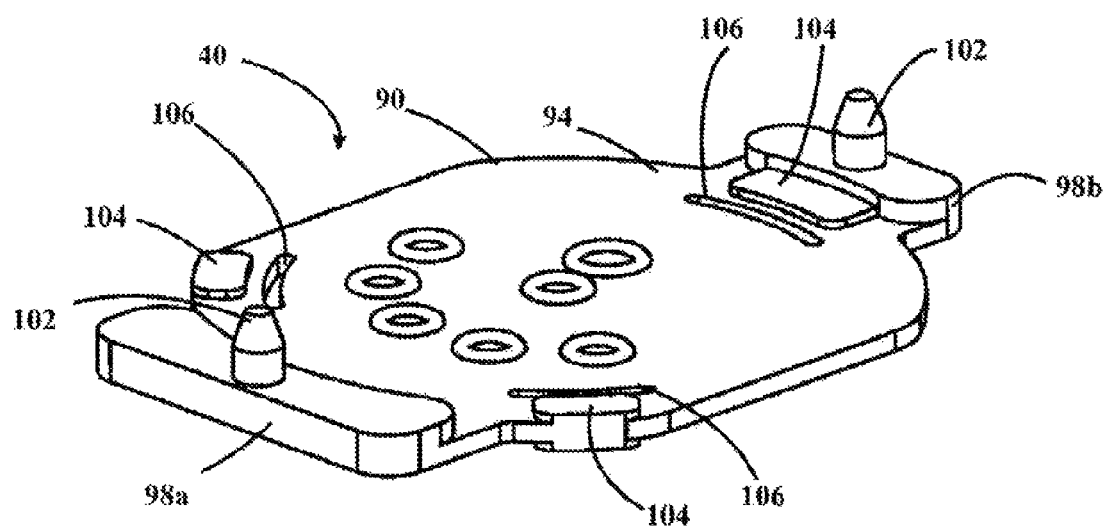
Figure 9C:
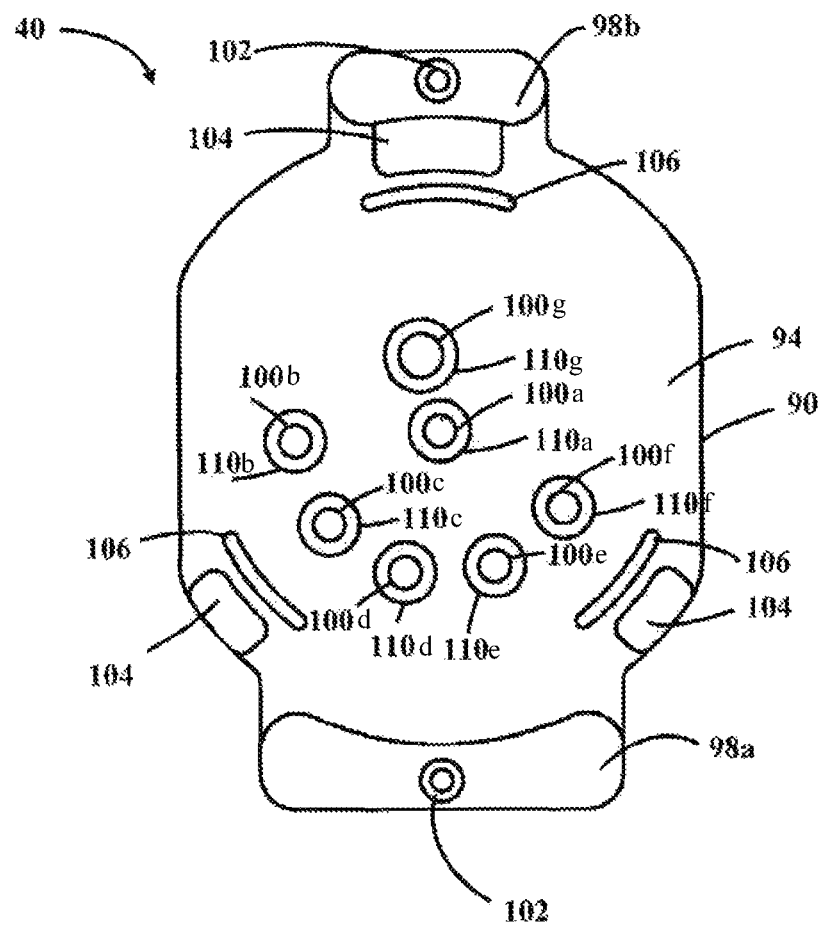
Figure 9D:
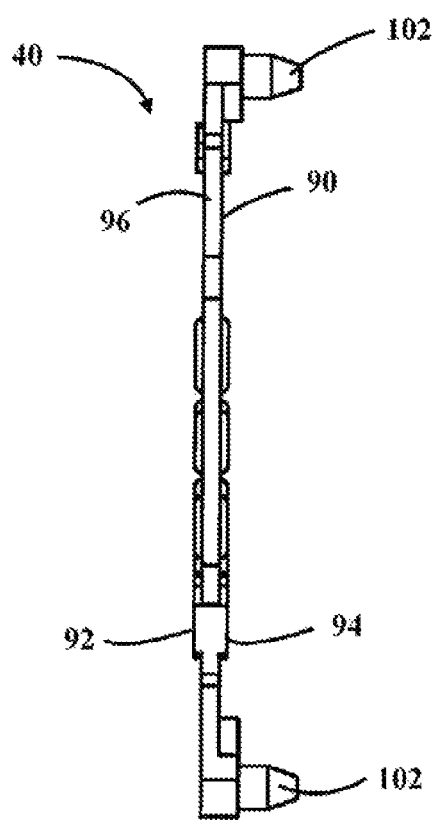
Figure 9E:
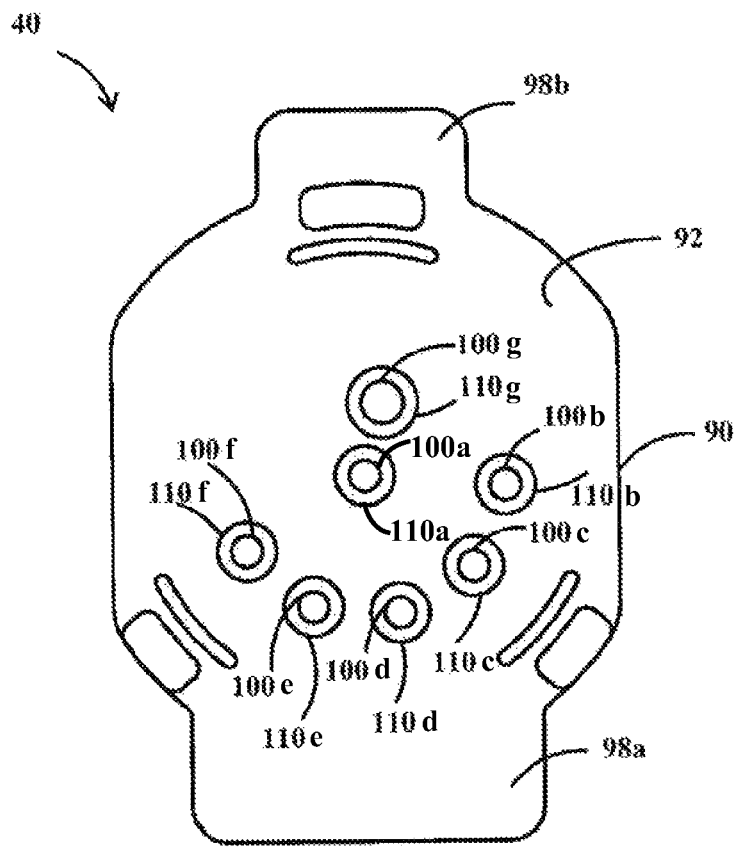
Figure 10A:
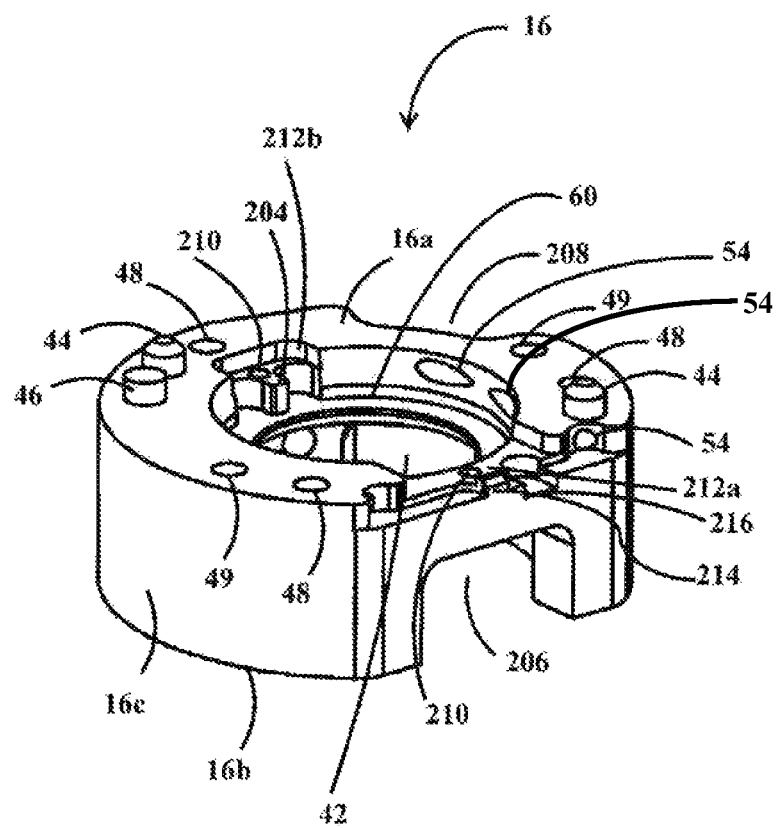
FIGS. 10A-10E show a top perspective, bottom perspective, top, side, and bottom views, respectively, of an exemplary manifold mount that may be used with the rotary shear valve of FIG. 1.
Figure 10B:
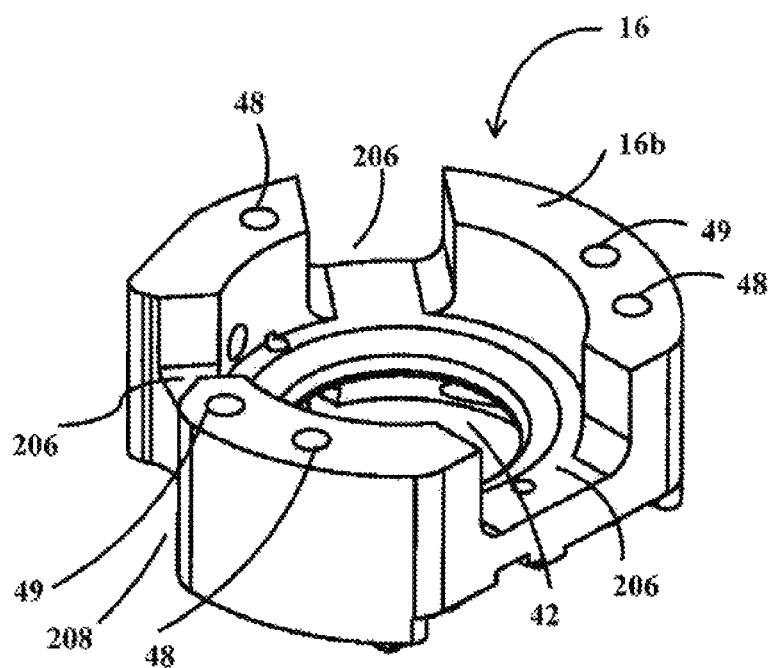
Figure 10C:
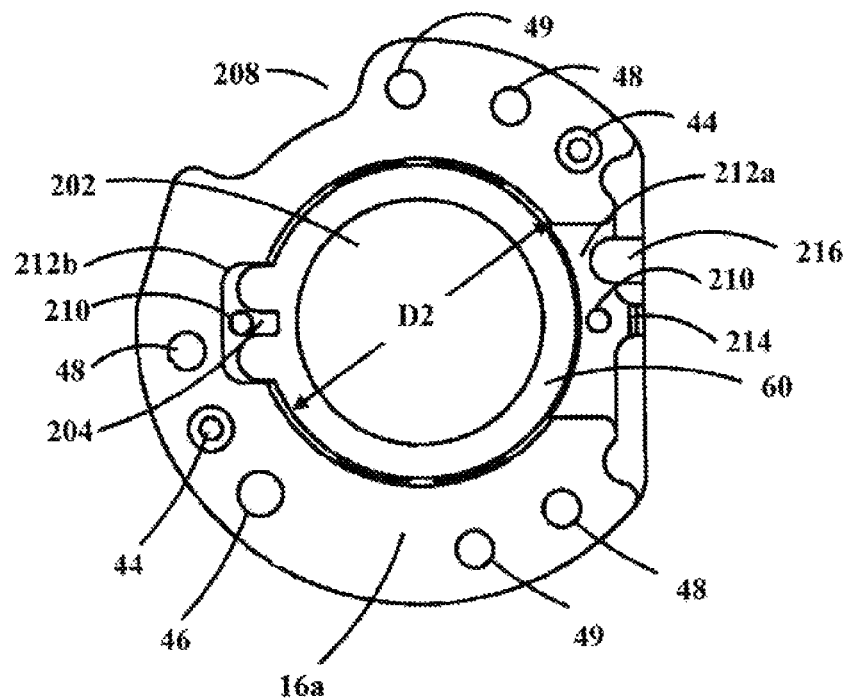
Figure 10D:
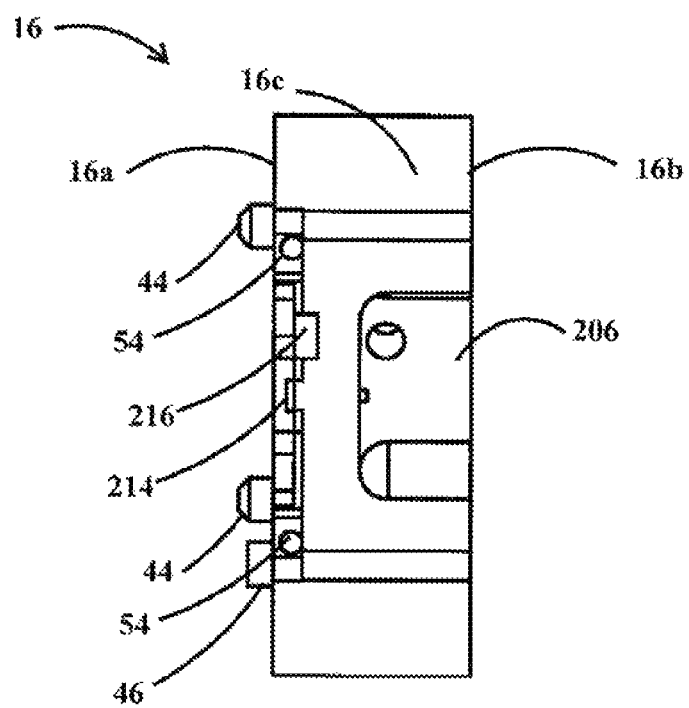
Figure 10E:
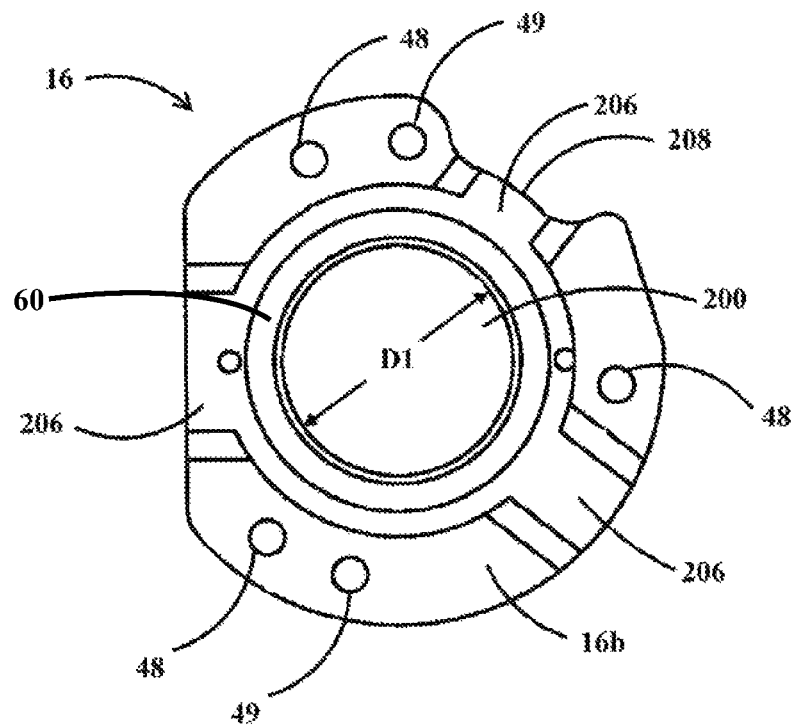

As shown in FIGS. 8B, 8D, and 8E, the bottom surface 76 includes a sealing face 76a that contacts the top surface or sealing face of the rotor 18. As shown, the sealing face 76a is generally circular or disc-shaped and is located in a center region of the bottom surface 76. An annular recessed surface 76b is provided around the outer periphery of the bottom surface 76. The shape and size of the annular recessed surface 76b generally conforms to the valve housing rim 60 upon which the stator 20 is seated.

As shown in the illustrated embodiment, three contact points 70 are provided at predetermined locations around the periphery of the bottom surface 76. In one embodiment, imaginary straight lines connecting the three contact points 70 may be located approximately 120 degrees apart from one another around the periphery of the stator 20 (i.e., imaginary straight lines connecting the three contact points form an equilateral triangle). In some embodiments, imaginary straight lines connecting the three contact points 70 may define an acute isosceles triangle, wherein the two angles having the same measure (i.e., the major angles) are between about 65 degrees and about 85 degrees. In yet other embodiments, the three contact points 70 define a scalene triangle, having no equal angles between the three contact points, and the periphery distance between any two of the three contact points is not equal. In one embodiment, two of the three contact points are between about 110 degrees and about 165 degrees from the other of the three contact points (e.g., contact point 70a of FIG. 8C) around the periphery of the stator.

As shown, the contact points 70 may include an extension of the sealing face 76a and extend into the recessed surface 76b. As such, the contact points 70 form raised or high points in the annular recessed surface 76b for contacting the valve body rim 60. The height of the contact points is sufficient to ensure that only the three contact points contact the valve body rim 60. Alternatively, the contact points may include a stand-alone structure.

The size and shape of the three contact points 70 may vary. In the illustrated embodiment, the contact points 70 are shown as substantially rectangular in shape. Preferably, the size of the contact points 70 is limited so that three single and distinct points of contact are made (e.g., a substantially zero dimension point)—as opposed to a continuous contact around portions or the entire periphery. Preferably, the size of the three contact points 70 on the stator 20 encompasses the area where force is applied by the gasket 40. In one exemplary embodiment, the length and width of each contact point 70 is about 0.5 mm to about 6 mm and the height is about 0.05 mm to full stator thickness. The three contact points 70 are designed to contact the valve housing rim 60 when the stator 20 is seated. Having three predefined contact points 70 helps control valve performance and minimize warping of the stator 20.

The stator 20 is positioned and oriented within the valve body 12 via a controlled outside diameter (OD) and a "clocking" or alignment feature 84. As shown, the alignment feature 84 may include one or more notches extending radially into the side wall 78 of the stator 20. A corresponding stator orientation feature or arm 204 (see e.g., FIGS. 5A and 10C) on the manifold mount 16 mates with the notch 84 to ensure proper positioning and orientation of the stator 20 in the rotary shear valve 10. In the illustrated embodiment, the alignment feature 84 is located at one of the contact points 70 (more specifically, 70a in FIG. 8C). In an alternate embodiment, the alignment feature 84 may be located in the side wall 78 of the stator 20 at a location that does not include a contact point.

As shown in FIGS. 8A, 8C, and 8D, an embodiment of the stator 20 may include one or more ledges 82 formed by cut-outs in the top surface 74. The illustrated embodiment shows two ledges 82 positioned on opposite sides of the stator 20 and extending generally parallel to one another. The ledges 82 may receive a retention system or retaining member 50, as shown and described in more detail with respect to FIGS. 6A and 6B. The retaining member 50 and ledges 82 are used for alignment and to hold the stator 20 in place in the valve body 12. As shown, there is no other structure of the valve body 12 for holding the stator 20 in place. In the illustrated embodiment, the stator 20 of the rotary shear valve 10 is loaded from the outside of the valve body 12. As such, a retaining mechanism 50 is advantageous to hold the stator 20 in place when the rotary shear valve 20 is not connected/mounted to another structure (e.g., a manifold 144 as shown in FIG. 15). When inserted through holes 54 in the manifold mount 16, the legs 52b of retaining member 50 contact the ledges 82 of the stator 20 to retain the stator 20 in the valve 10 and prevent the spring force being asserted upward on the stator 20 via the rotor 18/rotor spring 30 from pushing the stator 20 out of the valve body 12.

This feature improves assemblability and provides a rotary shear valve 10 having a modular design. This modular design allows for easy repair or replacement of the rotary shear valve 10. Conventional designs may have the stator attached to the manifold with epoxy. In the case of a failed valve (e.g., leaking valve), the entire rotary shear valve and manifold require replacement. This new design allows the rotary shear valve 10 to be removed and repaired/replaced without replacement of the manifold. This simplifies and reduces the cost for maintenance, since the manifold does not require replacement and/or the valve 10 may be repaired and re-installed.

In an embodiment having ledges 82, none of the three contacts points 70 is provided under a ledge 82. A contact point 70 may be provided in close proximity to one end of a ledge 82. In one embodiment shown, one contact point 70a may be provided substantially equal distance between first ends of the two ledges 82, and each of the other two contact points 70b, 70c may be provide proximate a second end of each of the two ledges 82 (see e.g., FIG. 8C).

During operation, the stator 20 is loaded on its top surface 74 by the compression force exerted by, for example, a gasket 40. In some embodiments, the compression force on gasket

40 may be generated by the clamping/bolting of the rotary shear valve 10 to a manifold (or other structure). This top loading by the gasket 40 on the stator 20 seats the three contact points 70 of the stator 20 on the valve body rim 60 at three predetermined or predefined points.

Figure 19:
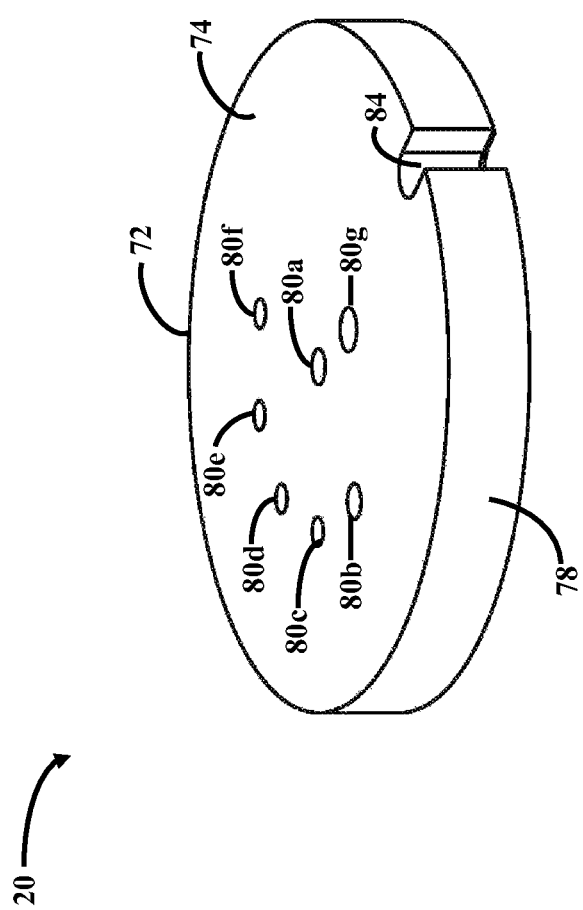
FIG. 19 shows another embodiment of the stator.

FIG. 19 shows another embodiment of the stator without ledges. The stator otherwise includes the same structure and features as described with respect to FIGS. 8A-8E.

FIG. 9A-9E show an exemplary gasket 40 that may be used with the rotary shear valve 10 of FIG. 1. The gasket 40 is a mechanical seal that fills the space between the mating surfaces of the stator 20 and a mounting structure. In some embodiments, the mounting structure includes an IMT fluid manifold 144. In the illustrated embodiment, the gasket 40 makes a seal between the top of the ceramic stator 20 and the acrylic face of manifold 144 to which the rotary shear valve 10 may be mounted (see e.g., FIGS. 15 and 18).

The gasket 40 includes a body or web 90, a top surface 92, a bottom surface 94, and a side wall 96. As shown, the size and shape of the gasket web 90 preferably conforms to the top surface 74 of the stator 20. The gasket material preferably has some degree of yielding such that the gasket 40 is able to deform and tightly fill the space between the stator 20 and the IMT module 144, including any slight irregularities in either structure. For example, the gasket material may comprise paper, rubber, synthetic rubber (thermosets), silicone, metal, cork, felt, neoprene, fiberglass, a plastic polymer, thermoplastics, and the like. In one embodiment, the gasket material is an elastomer and the gasket 40 comprises an injection molded piece. In one embodiment, the gasket 40 comprises a fluorocarbon (also referred to as fluoroelastomer) material, such as Viton®.

One or more tabs may extend from the gasket web 90 to align the gasket 40 over the stator 20 in the valve body 12. In the illustrated embodiment, two tabs 98a, 98b may be provided. The two tabs 98a, 98b may vary in shape and size to ensure proper alignment of the gasket 40 in the valve body 12. For example, in the illustrated embodiment, tab 98a is larger than tab 98b.

As shown, the gasket 40 has one or more pins 102 to locate and orient the gasket 40 on the valve body 12. In the illustrated embodiment, the gasket 40 has two location/orientation pins 102. The pins 102 may be received in holes 210 in the manifold mount 16 (see e.g., FIGS. 10A-10E). As shown, the distal ends of pins 102 may be tapered or conical in shape to facilitate insertion of the pins 102 into holes 210 in the manifold mount 16.

The gasket 40 includes a plurality of fluid ports or through holes 100 that correspond in number and location to the fluid ports 80 on stator 20 (FIG. 8A). As shown, the ports 100 are formed in a center region of the gasket 40. In the illustrated embodiment, for example, the gasket 40 may include seven fluid ports, including: center common port 100a; sample port 100b; vent 1 port 100c; Standard A port 100d; Standard B port 100e; vent 2 port 100f; and a waste port 100g (see FIG. 9A).

As shown, the gasket 40 also include a plurality of sealing features 110 that create a fluidic seal when compressed during assembly between the stator 20 and a mounting structure (e.g., an IMT manifold 144 as shown in FIG. 15). In one embodiment, the sealing features comprise o-rings 110. In the illustrated embodiment, seven o-rings 110a-110g are provided proximate the fluid ports 100a-100g in the gasket 40 (see FIGS. 9C and 9E). In some embodiments, the o-rings 110 are formed integral with the gasket 40 and comprise the same material as the gasket 40. In an embodiment of the rotary shear valve 10 having a relatively thin stator 20 (e.g., less than about 3 mm), which is desirable to minimize the unmixable volume or dead volume of fluid on the supply side of the stator 20, the o-ring seal features 110 preferably require a minimum seal force to reduce thin stator deflection. In some embodiments, the seal force is between about 0.5N to about 10N per o-ring port. In one embodiment, the rotary valve seal force is about 2.5N per o-ring port. In some embodiments, stator deflection is equal to or less than three light bands.

The gasket 40 also includes three clamping pads 104. In operation, the clamping pads 104 may be compressed against a mounting structure (e.g., an IMT manifold 144 as shown in FIG. 15) and register the stator 20 against the mounting structure. The clamping pads 104 function to provide a clamping force on the top of the stator 20 to counteract and balance the rotor spring force acting on the bottom of the stator via the rotor 18, thereby preventing stator 20 from floating and helping to maintain a seal between the stator 20 and rotor 18. The clamping pads 104 may be formed on the top surface 92, or the bottom surface 94, or the top 92 and bottom 94 surfaces of the gasket 40. Preferably, the size and shape of the clamping pads 104 correspond to the size and shape of the three contact points 70 on stator 20. As shown, the clamping pads 104 may include a substantially rectangular shape.

The three clamping pads 104 are provided at predetermined locations around the outer periphery region of the gasket web 90. Preferably, the location of each clamping pad 104 on gasket 40 corresponds to and aligns with respective contact points 70 on the stator 20 such that, upon compression of the gasket 40, the clamping pads 104 apply a seating force directly above the stator contact points 70.

For example, in one embodiment, the three clamping pads 104 may be located 120 degrees apart from one another around the periphery of the gasket 40 (i.e., imaginary straight lines connecting the three contact points form an equilateral triangle). In some embodiments, imaginary straight lines connecting the three pads 104 may define an acute isosceles triangle, wherein the two angles having the same measure are between about 65 degrees and about 85 degrees. In yet other embodiments, the three pads 104 define a scalene triangle, having no equal angles between the three pads, and the periphery distance between any two of the three clamping pads is not equal. In one embodiment, two of the three pads are between about 110 degrees and about 165 degrees from the other of the three pads around the periphery of the stator.

Figure 18:
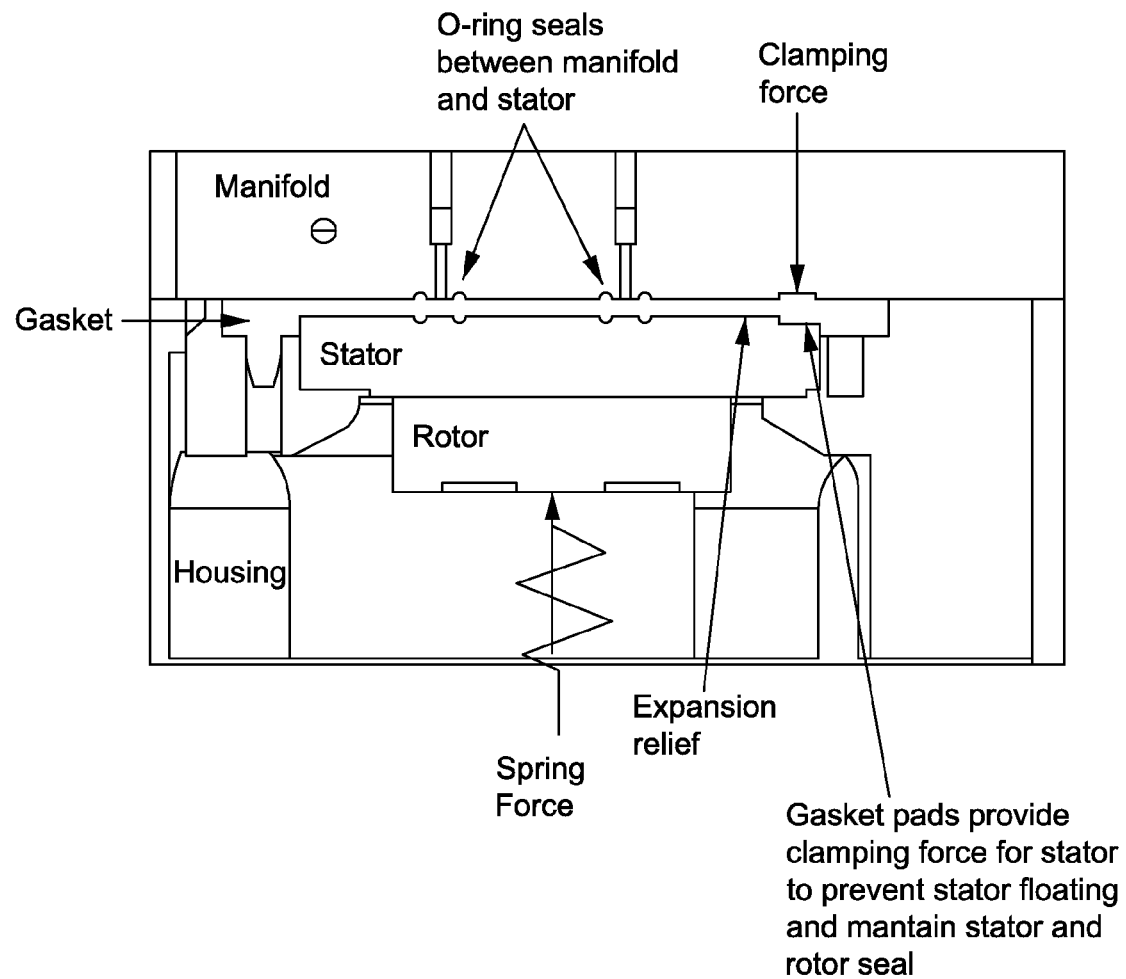
FIG. 18 is a cross section showing gasket compression.

In some embodiments, the gasket 40 serves both a sealing function and a clamping function (see FIG. 18). These two functions may be at odds with one another and may adversely affect each other. For example, in order for clamping features to generate large compression forces, a large amount of compression deformation is required. This compression deformation also generates relatively large expansions in the transverse direction. In contrast, gasket o-ring sealing features 110 require lower and controlled amounts of compression with precise positioning relative to the stator fluid ports 80. Movement or deformation of these features could cause o-ring seal failures or constrictions in the flow path due to o-ring misalignments. Embodiments of the present invention provide a gasket 40 having features that advantageously allow the two functions to be incorporated into a single component.

As shown, the gasket 40 may also include expansion reliefs 106. Expansion reliefs 106 allow the gasket clamping pads 104 to be compressed without adversely affecting the position or sealing capability of the gasket o-ring features 110. Preferably, the location of the expansion reliefs 106 is optimized to place them in areas where deformation caused by compression of the clamping pads 104 can be isolated from the sealing function features of the o-rings 110. As shown, the expansion reliefs 106 are located radially inward from the clamping pads 104. In the illustrated embodiment, one expansion relief 106 is located between each of the clamping pads 104 and the o-rings 110. In some embodiments, the expansion reliefs 106 are located in close proximity to the clamping pads 104, but do not touch the clamping pads 104. Location of the expansion reliefs 106 between the clamping pads 104 and the o-ring seal 110 accounts for differential expansion volume of the clamping pads 104 and o-ring features 110.

In some embodiments, the size and shape of the expansion reliefs 106 may be optimized to account for expansion of the gasket material in the transverse direction caused by compression of the clamping pads 104 and to isolate this transverse expansion from the sealing function features of the o-rings 110. The expansion reliefs 106 may comprise elongate openings in the gasket web 90 extending between the top surface 92 and the bottom surface 94. As shown, the expansion reliefs 106 may comprise elongate arc-shaped openings. In the illustrate embodiment, the convex surface of each elongate arc-shaped expansion relief 106 faces the clamping pad 104. In some embodiments, the expansion reliefs 106 have a length that is substantially equal to the length of the clamping pads 104. In some embodiments, the expansion reliefs 106 have a length that is longer than the length of the clamping pads 104. In some embodiments, the expansion reliefs 106 have a width that is between about 10% and about 50% of the width of the clamping pads 104. In some embodiments, the expansion reliefs 106 have a width that is between about 30% and about 40% of the width of the clamping pads 104. In some embodiments, the expansion reliefs 106 have rounded corners.

As described above, one function of the gasket 40 is to provide three clamping pads 104 for compression and seating the stator 20 in the valve body 12. Locating of the three clamping pads 104 of the gasket 40 in alignment with the three contact points 70 of the stator allows for relatively high or large compression forces without deformation or warping of the stator due to the equal and opposite forces acting on the top and bottom of the stator, which results in a substantially net zero force on the stator. As also described above, another function of the gasket 40 is to provide o-rings 110 sealing around the gasket ports 100 to form a seal between the stator 20 and a mounting structure (e.g., a fluid sampling manifold 144). Providing expansion reliefs 106 in the gasket 40 proximate the clamping pads 104, and between the clamping pads 104 and the sealing features 110, allows for transverse expansion of the clamping pads 104 without adversely affecting the sealing features of o-rings 110.

A gasket 40 comprising clamping pads 104 and expansion reliefs 106 results in a number of advantages. For example, both clamping and sealing features/functions can be incorporated and performed with one component. Use of a single component (as opposed to two separate components—one component to perform a clamping function and another component to perform a sealing function) provides both cost and time savings. There is only one part to purchase, transport, store, etc. instead of two; only one part to install rather than two parts; ease of maintenance and part replacement is improved since only one part is involved rather than two parts.

Another advantage of the present design and construction is that a smaller or very light rotor spring 30 may be used, thereby reducing and/or preventing ringing of the stator 20 and rotor 18. There are several factors that contribute to the ability to use a smaller or lighter spring, including the operating parameters (e.g., low pressure applications, including vacuum) and/or the arrangement of the stator 20 mounting within the valve body 12 and the loading of the stator 20 from the outside—as opposed to conventional arrangements that mount and load the stator inside the valve housing.

Many conventional rotary shear valves mount the stator in the valve body such that the valve body includes seating surfaces on both sides (e.g., top and bottom) of the stator. In such an embodiment, the rotor compression spring and rotor are used to press the stator upward into the valve body upper rim or seating surface to seat the stator and compress the gasket. At the same time, the gasket above the stator must still be compressed, typically using fasteners (e.g., bolts) that connect the rotary shear valve to a manifold, for example. This conventional gasket compression acts to provide a downward force to press the stator downward into the valve body lower rim or seating surface. This requires relatively high forces acting on both sides of the stator. In such an embodiment, a large or very strong spring (e.g., 20 pound spring or larger) is required. Also, a relatively thick stator is required due to the high forces. Another problem with this conventional design is that when two extremely flat articles—i.e., the highly polished sealing surfaces of the stator and the rotor—are compressed together, the surfaces may experience ringing (i.e., a sticking together of the two surfaces that is difficult to pull apart or move relative to one another). Ringing of the mating surfaces of the stator and rotor leads to another problem with conventional designs: the requirement that a much larger motor be used to generate enough torque to rotate the rotor with respect to the stator.

The design and construction of embodiments of the rotary shear valve 10 of the present invention avoid these problems and allow for the use of a smaller and/or lighter spring (e.g., less than about 15N) and a smaller motor (e.g., a drive torque less than about 5 mN-m). Also, a relatively thin stator (e.g., less than 3 mm), as compared to conventional stators, may be used due to the low forces. Loading the stator from the outside allows for the use of a smaller or lighter spring (e.g., a lower compression force of less than about 15N). Low operating pressure applications (e.g., valves operating at a pressure between 2.5 cm-Hg vacuum and 5.5 cm-Hg positive pressure) also allow for the use of a smaller or lighter spring (e.g., rotor spring force is about 10N). Use of a smaller or lighter spring helps reduce or eliminate ringing of the mating surfaces of the stator and rotor because less force is required between these two pieces (e.g., valve seal force is 2.5N per o-ring port). This, in turn, allows for the use of a smaller motor having less output torque. In addition to reducing the likelihood of ringing, a lower force between the stator and rotor may allow for a very thin layer of fluid to exist between the mating surfaces to provide some lubrication.

Embodiments of the present invention do not use the rotor spring 30 to load or seat the stator 20, or compress the gasket. Embodiments of the rotary shear valve 10 according to the present invention use the gasket 40 to top load whatever force is required on the top 74 of the stator 20 via the three raised clamping pads 104 to press the stator 20 such that the three raised contact points 70 on the bottom 76 of the stator 20 are in place on the valve body rim 60. This design has nothing to do with the rotor spring 30, so the rotor spring 30 may be a small or very light spring. The rotor spring 30 should be sized to provide sufficient force between the rotor 18 and the stator 20 to seal these mating surfaces, while still allowing rotation of the rotor 18 relative to the stator 20.

FIGS. 10A-10E are a top perspective, bottom perspective, top, side, and bottom views, respectively, of the manifold mount 16 of rotary shear valve 10 showing the additional features of the manifold mount 16. As shown, manifold mount 16 includes side wall 16c extending between manifold mounting face 16a and motor mounting face 16b. As shown, cavity 42 is defined in a center area of the manifold mount 16 and extends through from the manifold mounting face 16a and motor mounting face 16b.

Cavity 42 is designed to receive and orient rotor 18 and stator 20. As shown, cavity 42 includes a first diameter D1 (FIG. 10E) sized to receive rotor 18 and a second diameter D2 (FIG. 10C) sized to receive stator 20. First diameter D1 is defined by an inner edge of the valve body rim 60. The rotor 18 and rotor sleeve 19 are inserted into cavity 42 through a bottom opening 200 and are held in place during operation by the rotor spring 30. Stator 20 is inserted into cavity 42 through a top opening 202 and is seated on valve body rim 60 and held in place during operation by compression of gasket 40. In some embodiments, the distance between the contact surface of valve body rim 60 and manifold mounting face 16a is greater than the thickness of the stator and less than the combined height or thickness of the stator 20 and gasket 40. This allows for compression of the gasket 40 when the rotary shear valve 10 is mounted to, for example, a manifold, wherein the compression of gasket 40 seats the three contact points 70 of stator 20 in valve body rim 60.

In some embodiments, a stator orientation feature 204 is provided on manifold mount 16. As shown, stator orientation feature 204 may include an arm that is designed to interact and index with notch 84 on stator 20. Stator orientation feature 204 acts to ensure the proper alignment and orientation of stator 20 within manifold mount 16. As shown, the stator orientation feature 204 is recessed below the manifold mounting face 16a. In some embodiments, the depth that the stator orientation feature 204 is below the manifold mounting face 16a is substantially equal to the thickness of the gasket 40.

In some embodiments, one or more openings 210 are provided on manifold mount 16 for receiving location/orientation pins 102 of gasket 40. In the illustrated embodiment, two openings 210 are provided. As shown, the openings 210 are located approximately 180 degrees apart. Cut-outs 212 may also be provided in manifold mount 16. As shown, cut-outs 212 are sized and have a shape corresponding to tabs 98 of gasket 40. In operation, the pins 102 are inserted into openings 210, tab 98a is inserted in cut-out 212a, and tab 98b is inserted in cut-out 212b.

In embodiments having a stator retention system 50, the manifold mount 16 includes features for receiving and holding the stator retention system 50 in place on manifold mount 16. For example, in the illustrated embodiment, the manifold mount 16 includes holes 54 in the manifold mount 16 for receiving legs 52b of stator retention clip 52. As shown, the stator retention clip holes 54 extend substantially horizontally into cavity 42 at a location above the valve body rim 60 at a height substantially equal to the height or thickness of ledges 82 (FIGS. 8A and 8D) of stator 20. When the stator 20 is inserted into cavity 42 and onto valve body rim 60, the retention clip 52 may be inserted into holes 54 to engage ledges 82 and hold the stator 20 within valve body 12. The manifold mount 16 may also include a retention clip retainer 214 for engaging base 52a and securing the retention clip 52 to the manifold mount 16. A removal access 216 may be provided in manifold mount 16 to facilitate removal of the retention clip 52.

As shown in the exemplary embodiment, the manifold mount 16 may include a number of openings and/or cut-outs. For example, manifold mount 16 may include one or more openings 206 for allowing salt accumulations on the umbrella of rotor 18 and rotor sleeve 19 to fall out and away from the rotor/stator sealing interface. Also as shown, manifold mount 16 may include a drain cut-out 208 for receiving a drain (not shown).

As shown, the manifold mount 16 also includes one or more alignment posts 44 extending from the manifold mounting face 16a, a grounding pin 46 extending from the manifold mounting face 16a, a plurality of threaded holes 48 in the manifold mounting face 16a for mounting the manifold mount 16 to, for example, a manifold 144 (see FIG. 15), and a plurality of motor mounts 49 in the manifold mounting face 16a.

One exemplary use for a rotary shear valve 10 with three-point stator seating is in an in vitro diagnostic device 120 (FIG. 11) intended to duplicate manual analytical procedures such as pipetting, mixing, heating, and measuring spectral intensities to determine a variety of analytes in human body fluids. One such suitable device is the Dimension Vista® system manufactured by Siemens Healthcare Diagnostics.

Figure 11:
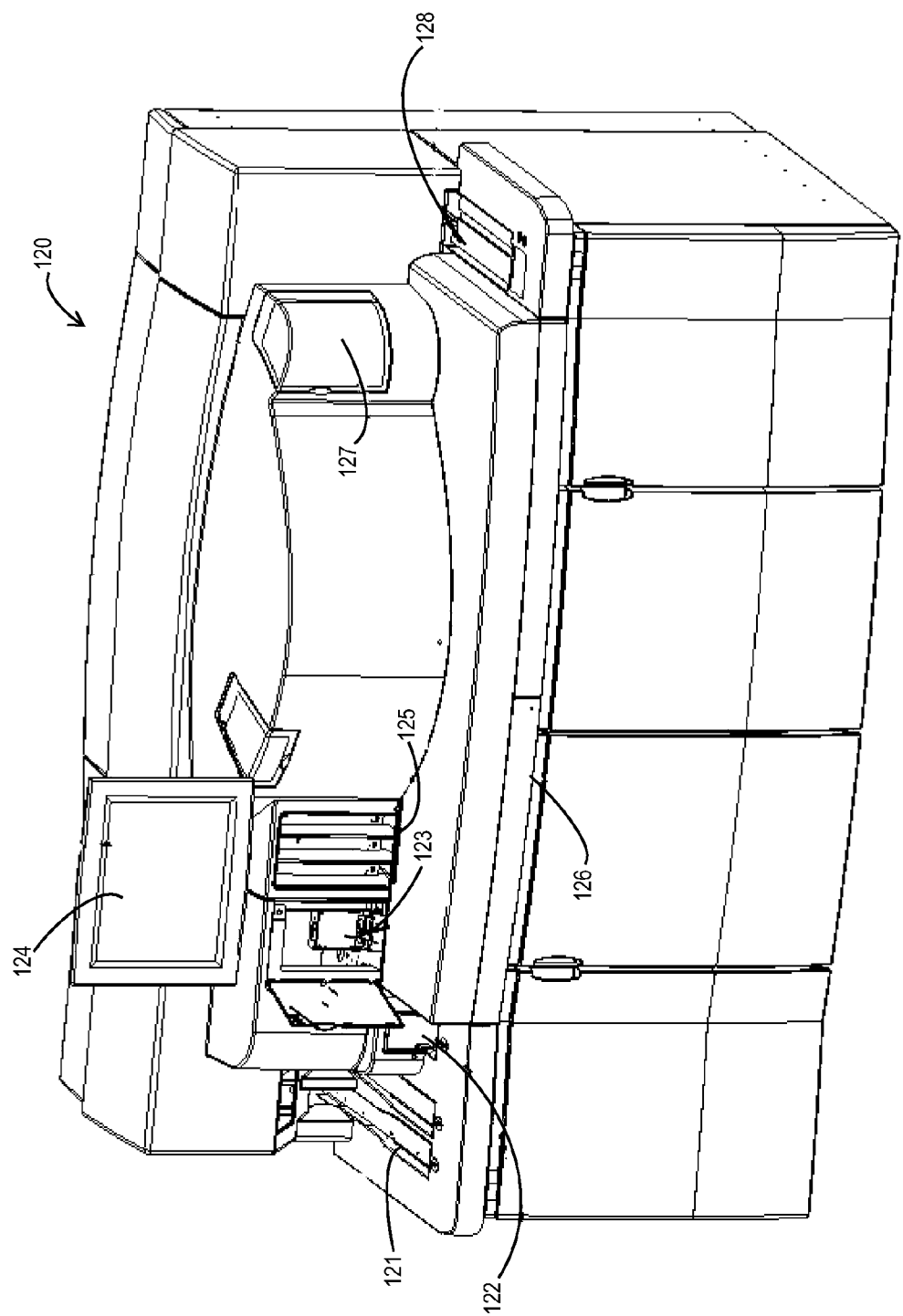
FIG. 11 is a perspective view of an exemplary diagnostic device in which the rotary shear valve may be employed.

FIG. 11 shows an exemplary diagnostic device 120 in which the rotary shear valve with three-point stator seating may be employed. As shown in FIG. 11, the diagnostic device includes, for example: sample rack lanes 121; STAT input lane 122; IMT system 123; display device (e.g., touch screen monitor) 124; reaction vessel loader 125; user input device (e.g., keyboard and mouse) 126; cuvette loader 127; and reagent loader 128. The diagnostic device illustrated in FIG. 11 may perform multiple operations, including assay measurements. Exemplary system operating pressure for such a device may range from 50 cm-Hg vacuum to 160 cm-Hg positive pressure.

In an exemplary assay measurement operation, a cuvette or reaction vessel may move to a reagent probe for the server where a reagent cartridge is located. The reagent probe aspirates reagent from the cartridge and dispenses it into the cuvette or vessel. A sample probe aspirates sample from an aliquot plate well and dispenses it into the cuvette or vessel. Reaction of sample in a cuvette may be measured either by a photometer or by a nephelometer, depending on the requested test. Reaction of sample in a reaction vessel may be read by a reaction vessel reader.

Measurement of electrolytes (e.g., sodium ($Na^+$), potassium ($K^+$), chloride ($Cl^-$)) may be performed in the IMT system 123. The IMT system 123 on the exemplary diagnostic device 120 provides for the potentiometric determination of sodium, potassium, and chloride using a flow-through sensor cartridge enclosing solid-phase electrodes. When an electrolyte test is requested, the IMT sampler probe (not shown) aspirates sample from an aliquot plate and dispenses it into the IMT port on the manifold where a dilution of the sample with a diluent is made using a fluid "chase" method. The pre-diluted, bulk, fluid standard solutions may be supplied to the sensors through a rotary shear valve 10 with fluid ports for, for example, Diluent Standard A (Std-A), Diluent Standard B (Std-B), Sample, and Air. The sample port may be rinsed with Diluent Std-A solution, for example, between samples. The diluted sample is then pulled through the IMT sensor (not shown) for measurement. The IMT probe may be rinsed after each aspirate-dispense action.

In one application, the IMT system 123 will process all serum and urine samples to obtain desired results. One goal of the exemplary diagnostic device IMT system 123 is to provide a robust system for rapidly processing high volumes of fluids, such as serum, plasma, and urine samples.

Figure 12:
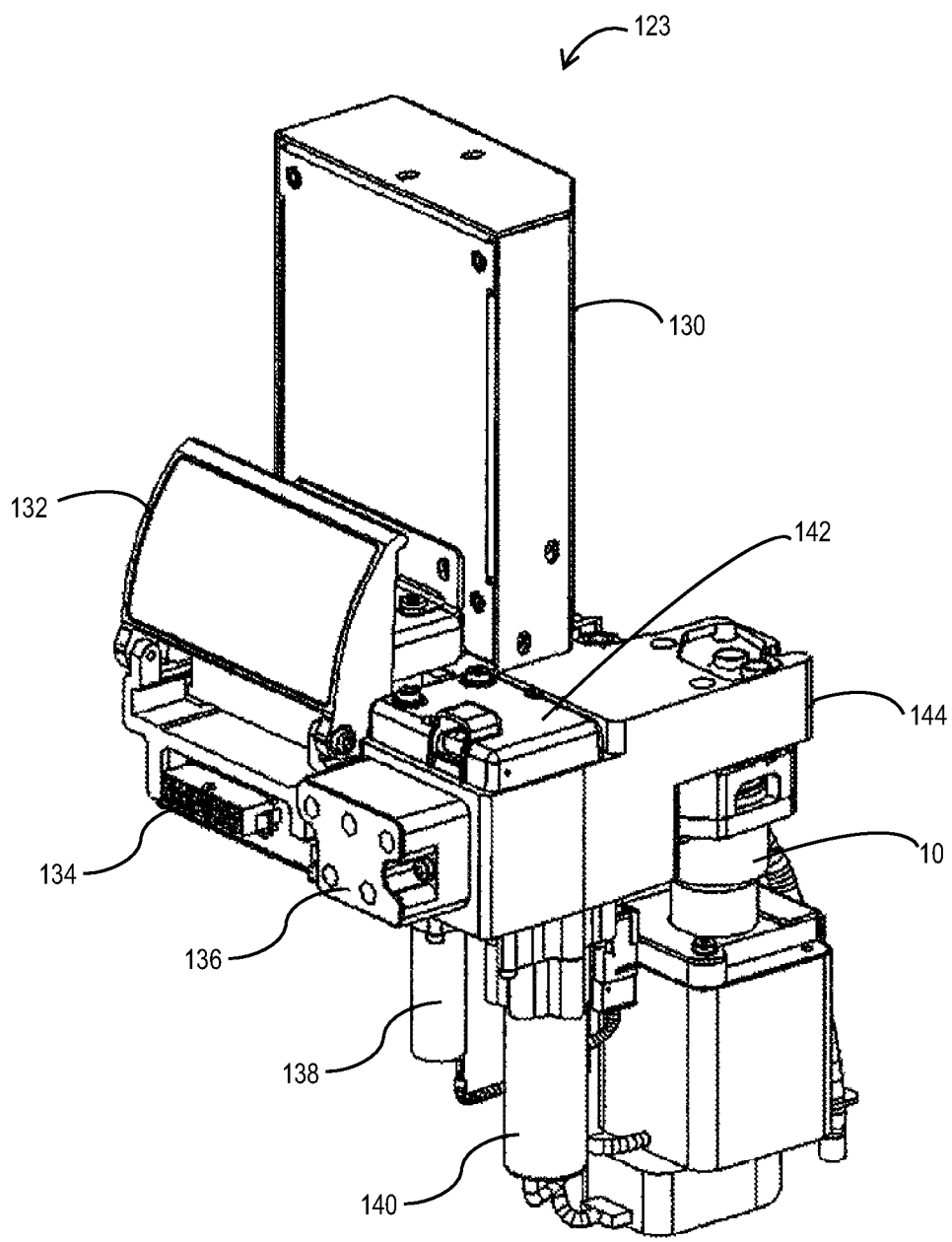
FIG. 12 is a perspective view of an exemplary IMT (integrated multi-sensor technology) module that is part of the diagnostic device of FIG. 11.

In one exemplary application, the rotary shear valve 10 may be used as part of an IMT system, which is shown and described in more detail with reference to FIGS. 12-15. As shown in FIG. 12, the IMT system 123 includes an electrolyte reader assembly 130, an actuator chip placement door 132, a module electrical cable connector 134, a fluids interface manifold 136, a 2-way solenoid valve 138, a solenoid pump 140, a pressure manifold 142, a manifold assembly 144, and a rotary shear valve 10.

Figure 13:
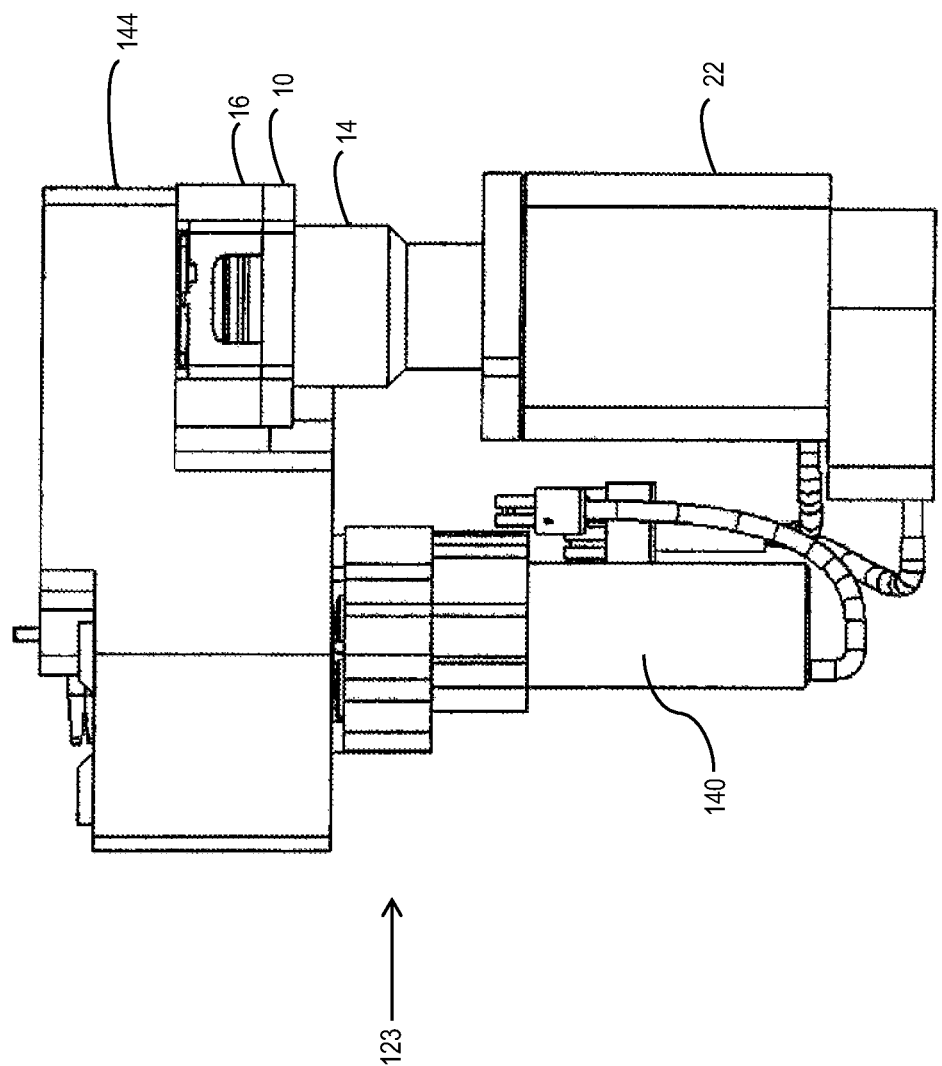
FIG. 13 is an end view of an exemplary rotary shear valve of FIG. 1 attached to a manifold of the IMT module of FIG. 12.
Figure 14:
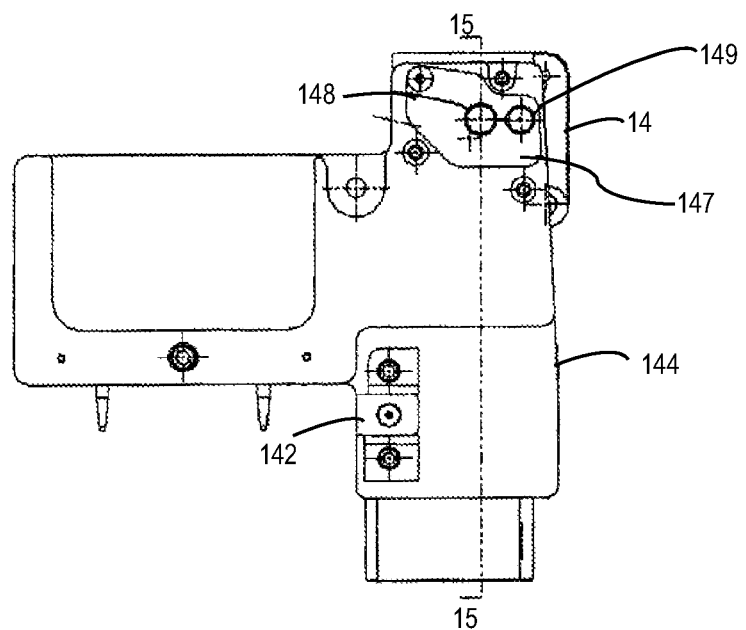
FIG. 14 is a top plan view of the exemplary manifold to which the rotary shear valve may be connected/mounted.

FIG. 13 shows an end view of the IMT system 123 showing the rotary shear valve 10 mounted to the manifold assembly 144. FIG. 14 is a top plan view of the manifold assembly 144. As shown in FIG. 14, manifold 144 includes a sample port 148 and a vent port 149.

FIG. 15 is a cross sectional view of the manifold assembly 144 and rotary shear valve 10 taken along line 15-15 of FIG. 14. As shown in FIG. 15, the output shaft 24 of motor 22 is connected to the rotor drive shaft 23 via a slot and tongue connection. A drive shaft dog bone of the rotor drive shaft 23 is coupled to the rotor sleeve 19 at a rotor sleeve pocket. The spring 30 and thrust bearing 32 are disposed about the rotor drive shaft 23 and reside within cup 28. The rotor spring 30 pushes upward on the rotor 18 and forms a seal between the seal face of the ceramic rotor 18 and the seal face of the ceramic stator 20. The stator 20 is top loaded, pushed downward and seated on valve housing rim 60 by the compression force of the gasket 40, which is disposed between the ceramic stator 20 and the acrylic bottom of the manifold assembly 144.

Figure 16:
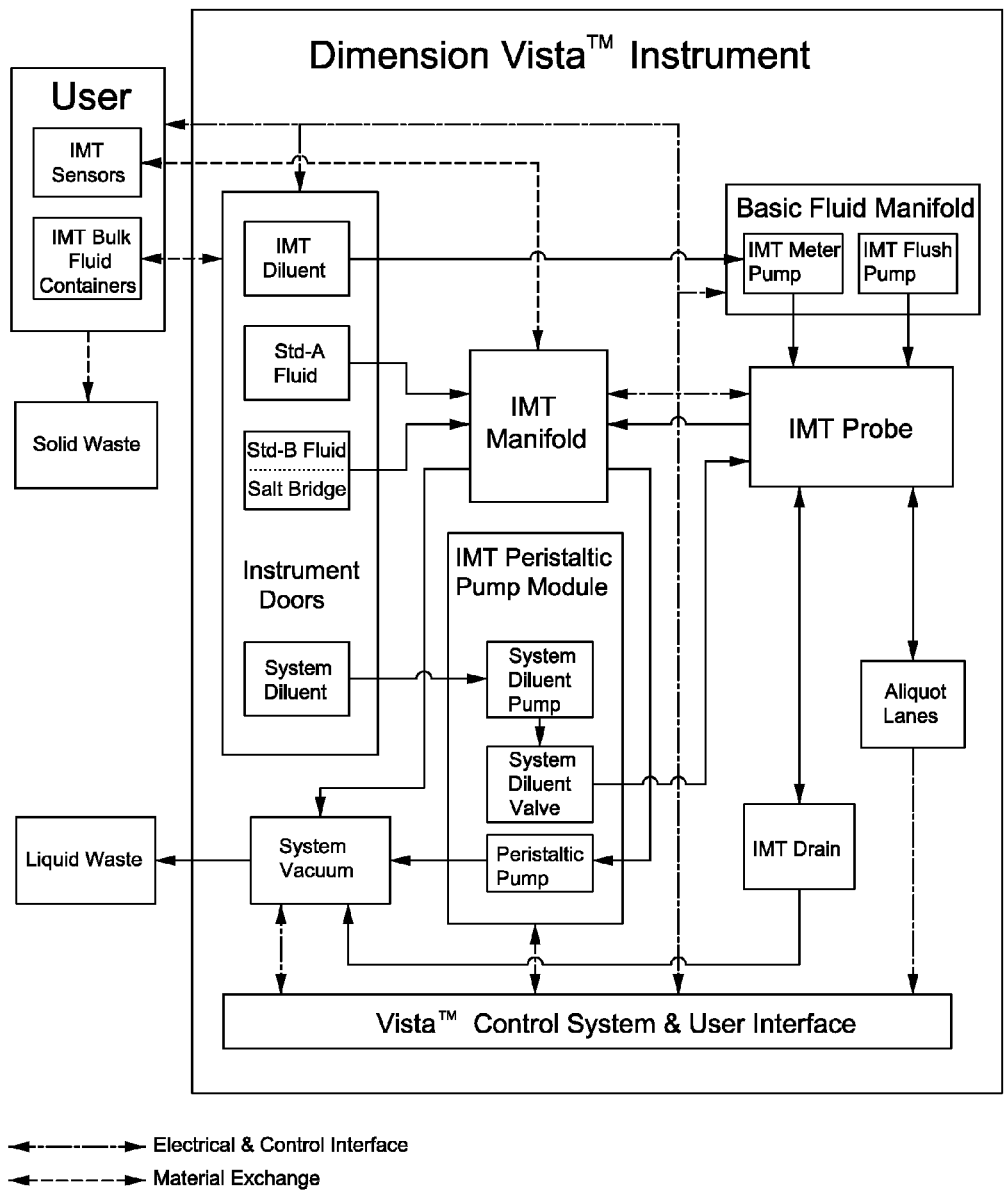
FIG. 16 illustrates an exemplary IMT system functional interface block diagram.
Figure 17:
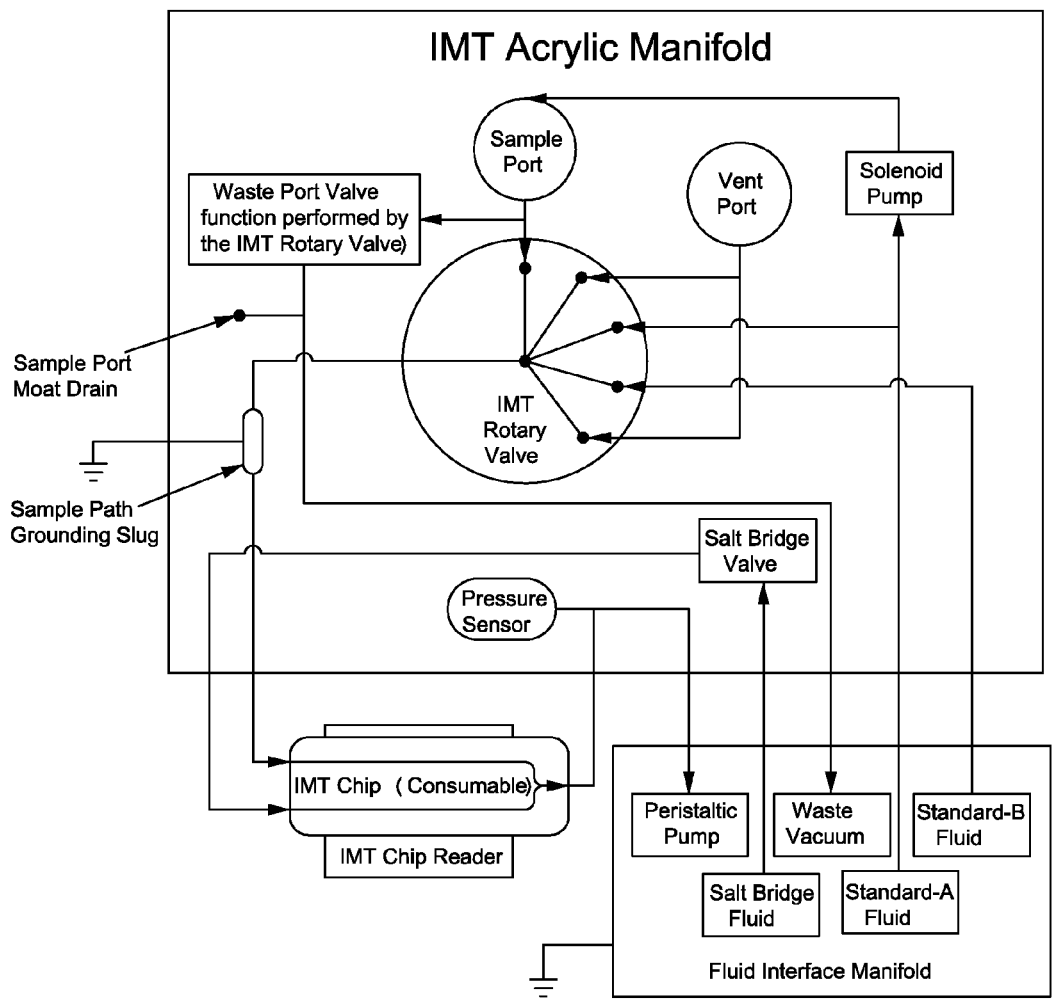
FIG. 17 illustrates an exemplary IMT system fluidic schematic.

FIG. 16 illustrates an exemplary IMT system 123 functional interface block diagram. FIG. 17 illustrates an exemplary IMT module fluidic schematic. As shown, the IMT manifold 144 provides the fluidic channels for the Diluent Standard A and Diluent Standard B, Diluent Salt Bridge, vent air, sample fluids, and liquid waste. The IMT manifold 144 supports the fluidic hardware used to control the routing of fluids through the manifold 144. In one embodiment, the manifold 144 is machined from three layers of acrylic plastic. The layers are machined prior to bonding to form the internal pathways of the manifold 144. A stainless steel fluid grounding pin 46 (see FIGS. 4A and 4B) is imbedded in the acrylic to provide an electrical ground to fluid in the sample channel. Post-bonding machining operations may be used to create the external manifold features after the bonding process. Threaded inserts, locating pins, and the IMT fluid pins are included.

During sample/standards processing, the fluids are selectively directed to the sample pathway and into the IMT sensor cartridge sample channel with the rotary shear valve 10. Fluids are drawn into the manifold 144, for example, with vacuum pressure created by a peristaltic pump module or a vacuum waste system. Air segments in the fluid streams are introduced by momentarily moving the rotary shear valve 10 to a vent location to access ambient air. Standard A solution is pumped by the Standard A solenoid pump into the sample port in aliquots to rinse the sample port. In the illustrated embodiment, Standard A is the only fluid moved within the manifold 144 using positive pressure. The flow rate of the Standard A flush is regulated by the diameter of the outlet path from the Standard A flush pump. A salt bridge solenoid valve allows salt bridge solution to enter the salt bridge channel of the IMT sensor cartridge. The manifold 144 has a fluid overflow retention area 147 (FIG. 14), referred to as the "moat." The moat 147 may be drained by a small diameter parasitic port that connects to the main waste channel of the manifold 144.

The IMT rotary valve is a stepper controlled ceramic rotary shear valve 10 in accordance with one embodiment of the present invention. The main fluidic components of the valve are a highly polished ceramic rotor 18 and stator 20. The rotor 18 and stator 20 are forced together by a compression spring 30 that pushes against a thrust bearing 32. In the exemplary embodiment, the rotor 18 has two slots: the selector slot 64*a*;

and the waste slot 64*b* (see e.g., FIG. 7A). Also in the exemplary embodiment, the stator 20 has seven fluid ports, including: center or common port; sample port; vent 1 port; Standard A port; Standard B port; vent 2 port; and a waste port. Fluids are directed from one stator port to another by positioning the slots 64 in the rotor 18 to connect the desired stator ports 80.

Although the invention has been described with reference to exemplary embodiments, it is not limited thereto. Those skilled in the art will appreciate that numerous changes and modifications may be made to the preferred embodiments of the invention, and that such changes and modifications may be made without departing from the true spirit of the invention. It is therefore intended that the appended claims be construed to cover all such equivalent variations as fall within the true spirit and scope of the invention.

What is claimed is:

1. A rotary shear valve comprising:
   a valve body comprising a motor mount end and a manifold mount end, and a cavity extending between the motor mount end and the manifold mount end;
   a valve body rim in the cavity;
   a disc-shaped rotor rotatably mounted in the valve body, the rotor comprising:
      one or more slots in a top surface; and
      a rotor sealing face on the top surface;
   a disc-shaped stator mounted in the valve body, the stator comprising:
      a top surface and a bottom surface;
      one or more ports extending between the top surface and the bottom surface;
      a stator sealing face on the bottom surface, wherein the stator sealing face is in sliding and sealing contact with the rotor sealing face; and
      an annular recess in an outer periphery of the bottom surface of the stator; and
   three predefined contact points defined between the stator annular recess and the valve body rim, wherein the stator only contacts the valve body rim at the three contact points.

2. The rotary shear valve of claim 1, wherein the three predefined contact points are integrally formed with the stator.

3. The rotary shear valve of claim 2, wherein the three predefined contact points are formed as extensions of the bottom surface of the stator into the annular recess.

4. The rotary shear valve of claim 1, wherein the three predefined contact points are formed as high points on the annular recess of the stator.

5. The rotary shear valve of claim 1, wherein the three predefined contact points are substantially 120 degrees apart around the outer periphery of the bottom surface of the stator.

6. The rotary shear valve of claim 1, wherein the three predefined contact points are integrally formed with the valve body rim.

7. The rotary shear valve of claim 1, wherein imaginary lines connecting the three predefined contact points form an isosceles triangle, wherein a second contact point and a third contact point are substantially equal distance from a first contact point, wherein the two angles having the same measure are between about 65 degrees and about 85 degrees.

8. The rotary shear valve of claim 1, further comprising three clamping pads for contacting the top surface of the stator, wherein the three clamping pads correspond to, and are aligned with, the three predefined contact points such that forces on the stator top surface and the stator bottom surface are equal and oppose, and substantially cancel one another out.

9. The rotary shear valve of claim 8, further comprising a gasket, the gasket comprising:
   a gasket web, wherein the three clamping pads are integrally formed with the gasket web, and the three clamping pads contact the top surface of the stator above the three predefined contact points.

10. The rotary shear valve of claim 1, wherein the stator has a thickness of less than about 3 mm.

11. The rotary shear valve of claim 1, further comprising an alignment feature to ensure proper alignment and orientation of the stator in the valve body, the alignment feature comprising:
    a notch on the stator; and
    an arm on the valve body,
    wherein the arm is received within the notch.

12. A rotary shear valve comprising:
    a valve body comprising:
      a motor mount end;
      a manifold mount end;
      a cavity extending between the motor mount end and the manifold mount end; and
      a valve body rim having an inner diameter and a valve body rim seating surface;
    a motor mounted to the motor mount end, the motor having an output shaft extending into the cavity;
    a cup disposed within the cavity;
    a spring disposed within the cup, a first end of the spring contacting the cup;
    a thrust bearing disposed on a second end of the spring;
    a disc-shaped rotor rotatably disposed within the valve body, the rotor comprising a rotor top surface having a rotor sealing face, a rotor sleeve, and a rotor drive shaft, wherein the rotor drive shaft extends through the thrust bearing, the spring, and the cup, a first end of the rotor drive shaft is connected to the motor output shaft, the rotor sleeve contacts the thrust bearing, and the rotor sealing face is disposed within the inner diameter of the valve body rim;
    one or more fluid slots in the top surface of the rotor;
    a disc-shaped stator mounted in the valve body, the stator comprising:
      a stator top surface and a stator bottom surface;
      a plurality of fluid ports extending between the stator top surface and the stator bottom surface;
      a stator sealing face on the stator bottom surface, wherein the stator sealing face is in sliding and sealing contact with the rotor sealing face; and
      an annular recess in an outer periphery of the stator bottom surface; and
    three contact points defined between the stator annular recess and the valve body rim seating surface, wherein the stator only contacts the valve body rim at the three contact points.

13. The rotary shear valve of claim 12, wherein the valve body further comprises:
    a motor mount comprising a motor mount first end, a motor mount second end, and a motor mount cavity extending between the motor mount first end and the motor mount second end; and
    a manifold mount comprising a manifold mount first end, a manifold mount second end, and a manifold mount cavity extending between the manifold mount first end and the manifold mount second end, wherein the manifold mount first end is connected to the motor mount second end.

14. The rotary shear valve of claim 12, further comprising a gasket in contact with the stator top surface, the gasket comprising:
    a gasket body, the gasket body generally corresponding in size and shape to the stator;
    a plurality of fluid ports, the gasket fluid ports corresponding in number and location to the stator fluid ports;
    an o-ring around a perimeter of each of the gasket fluid ports; and
    three clamping pads disposed near the periphery of the gasket body, wherein the three clamping pads correspond to, and are aligned with, the three contact points of the stator when the gasket is in contact with the stator top surface.

15. A stator for use in a rotary shear valve comprising:
    a disc-shaped body having a top surface, a bottom surface, and a side wall extending between the top surface and the bottom surface;
    one or more ports extending between the top surface and the bottom surface;
    a disc-shaped sealing face in a center region of the bottom surface;
    an annular recess in an outer periphery of the bottom surface and surrounding the disc-shaped sealing face; and
    three predefined contact points in the annular recess, the three contact points raised above the annular recess.

16. The stator of claim 15, wherein the three predefined contact points further comprise three predefined extensions of the disc-shaped sealing face into the annular recess.

17. The stator of claim 15, wherein a distance between the top surface of the disc-shaped body and the sealing face is greater that the distance between the top surface of the disc-shaped body and the annular recess.

18. The stator of claim 15, wherein the distance between the top surface of the disc-shaped body and the contact points is substantially equal to the distance between the top surface of the disc-shaped body and the sealing face.

19. The rotary shear valve of claim 15, wherein the three predefined contact points are substantially 120 degrees apart around an outer periphery of the stator.

20. The rotary shear valve of claim 15, wherein imaginary lines connecting the three predefined contact points form an isosceles triangle, wherein a second contact point and a third contact point are substantially equal distance from a first contact point, wherein the two angles having the same measure are between about 65 degrees and about 80 degrees.

* * * * *